US009134293B2

(12) United States Patent
Balkwill et al.

(10) Patent No.: US 9,134,293 B2
(45) Date of Patent: Sep. 15, 2015

(54) CANCER MARKER AND THERAPEUTIC TARGET

(75) Inventors: Frances Balkwill, London (GB); Violet Slettenaar, London (GB); Julia Wilson, London (GB); Yaohe Wang, London (GB); Tiziana Schioppa, London (GB)

(73) Assignee: Cancer Research Technology Ltd., London (GB)

( * ) Notice: Subject to any disclaimer, the term of this patent is extended or adjusted under 35 U.S.C. 154(b) by 1076 days.

(21) Appl. No.: 12/679,002

(22) PCT Filed: Sep. 18, 2008

(86) PCT No.: PCT/GB2008/003160
§ 371 (c)(1),
(2), (4) Date: Jun. 25, 2010

(87) PCT Pub. No.: WO2009/037454
PCT Pub. Date: Mar. 26, 2009

(65) Prior Publication Data
US 2010/0278844 A1    Nov. 4, 2010

(30) Foreign Application Priority Data

Sep. 18, 2007   (GB) .................................. 0718167.0

(51) Int. Cl.
| *A61K 39/395* | (2006.01) |
| *G01N 33/574* | (2006.01) |
| *G01N 33/576* | (2006.01) |
| *G01N 33/50*  | (2006.01) |
| *A61K 31/00*  | (2006.01) |

(52) U.S. Cl.
CPC ............ *G01N 33/5005* (2013.01); *A61K 31/00* (2013.01); *G01N 33/574* (2013.01); *G01N 2800/52* (2013.01); *G01N 2800/56* (2013.01)

(58) Field of Classification Search
None
See application file for complete search history.

(56) References Cited

U.S. PATENT DOCUMENTS 5,342,947 A * 8/1994 Lackey et al. .................... 546/41
5,786,158 A * 7/1998 Artavanis-Tsakonas et al. ............. 435/7.23

FOREIGN PATENT DOCUMENTS

| EP | 1 661 889 A1 | 5/2006 |
| EP | 1 688 436 A1 | 8/2006 |
| WO | 99/15666 A2 | 4/1999 |
| WO | 00/42074 A1 | 7/2000 |
| WO | 02/067771 A2 | 9/2002 |
| WO | WO02/067771 | * 9/2002 |
| WO | 2004/082635 A2 | 9/2004 |
| WO | 2004/108717 A1 | 12/2004 |
| WO | WO2005/106471 | * 11/2005 |

OTHER PUBLICATIONS

Niwa et al (Cancer Research, 2004, vol. 64, pp. 2127-2133).*
The abstract of Slettenaar et al (Proc Amer Assoc Cancer Res, 2006, vol. 47, abstract 2810).*
Nakamura et al (Clinical Experimental Metastasis, published on-line Jul. 5, 2006, vol. 23, pp. 9-18).*
Acevedo et al., "Loss of Heterozygosity on Chromosome Arms 3p and 6q in Microdissected Adenocarcinomas of the Uterine Cervix and Adenocarcinoma in Situ", Cancer, Feb. 1, 2002, p. 793-802, vol. 94, No. 3.
Allen et al., "Chemokine: receptor structure, interactions, and antagonism", Annu Rev Immunol, 2007, p. 787-820, vol. 25.
Baatar et al., "CCR4-Expressing T Cell Tumors Can Be Specifically Controlled via Delivery of Toxins to Chemokine Receptors", The Journal of Immunology, 2007, p. 1996-2004, vol. 179.
Balkwill, F.R. "Cancer and the chemokine network", Nature, 2004, p. 540-550, vol. 4.
Balkwill, F.R. "Smoldering and polarized inflammation in the initiation and promotion of malignant disease", Cancer Cell, 2005, p. 211-217, vol. 7.
Balkwill. "The significance of cancer cell expression of the chemokine receptor CXCR4", Seminars in Cancer Biology, 2004, p. 171-179, vol. 14.
Bange et al. "Molecular targets for breast cancer therapy and prevention", Nature Medicine, 2001, p. 548-552, vol. 7, No. 5.
Berin et al., "Production of MDC/CCL22 by human intestinal epithelial cells", Am J Psysiol Gastrointest Liver Physiol, 2001, p. G1217-G1226, vol. 280.
Borrello et al., "Induction of a proinflammatory program in normal human thyrocytes by the RET/PTCI oncogene", PNAS, Oct. 11, 2005, p. 14825-14830, vol. 102, No. 41.
Braga et al., "Critical tumor-suppressor gene regions on chromosome 3p in major human epithelial malignancies: allelotyping and quantitative real-time PCR", Int J Cancer, 2002, p. 534-541, vol. 100.
Burger et al., "CXCR4: a key receptor in the crosswalk between tumor cells and their microenvironment", Blood, Mar. 1, 2006, p. 1761-1767, vol. 107, No. 5.
Cabioglu et al., "Chemokine receptor CXCR4 expression in breast cancer as a potential predictive marker of isolated tumor cells in bone marrow", Clinical & Experimental Metastasis, 2005, p. 39-46, vol. 22.
Condeelis et al. "Macrophages: Obligate Partners for Tumor Cell Migration, Invasion, and Metastasis", Cell, 2006, p. 263-266, vol. 124.

(Continued)

*Primary Examiner* — Karen Canella
(74) *Attorney, Agent, or Firm* — Kilpatrick Townsend & Stockton LLP

(57) ABSTRACT

Chemokine receptor CCR4 and its ligands CCL1 7 and CCL22 are used as markers for the identification and/or staging of cancer. The level of CCR4, CCL17 and CCL22 are found to increase during malignant tumor progression. CCR4, CCL17 and CCL22 are used as markers for the stratification of cancer patients according to their suitability for treatment with anti-cancer agents. Information of diagnostic character is provided by measuring the level of one or more of CCR4, CCL 17 and CCL22 present in a patient sample. Methods of treatment of cancer patients which agents that modulate the activity of CCR4, CCL17 and CCL22. Methods of screening for agents which modulate the biological activities of CCR4, CCL 17 and CCL22 provide anti-cancer agents.

18 Claims, 14 Drawing Sheets

(56) References Cited

OTHER PUBLICATIONS

Ferenczi et al., "Increased CCR4 Expression in Cutaneous T Cell Lymphoma", The Journal of Investigative Dermatology, Dec. 2002, p. 1405-1410, vol. 119, No. 6.

Fra et al., "Cutting Edge: Scavenging of Inflammatory CC Chemokines by the Promiscuous Putatively Silent Chemokine Receptor D6", The Journal of Immunology, 2003, p. 2279-2282, vol. 170.

Godiska et al., "Human Macrophage-derived Chemokine (MDC), a Novel Chemoattractant for Monocytes, Monocyte-derived Dendritic Cells, and Natural Killer Cells", J. Exp. Med., May 5, 1997, p. 1595-1604, vol. 185, No. 9.

Gordon, S. "Alternative activation of macrophages", Nature Reviews Immunology, Jan. 2003, p. 23-35, vol. 3.

Graham et al., "Chemokine scavenging by D6: a movable feast?", Trends in Immunology, 2006, p. 381-386, vol. 27, No. 8.

Hagemann et al., "Ovarian Cancer Cells Polarize Macrophages Toward a Tumor-Associated Phenotype", The Journal of Immunology, 2006, p. 5023-5032, vol. 176.

Imai et al., "Selective secretion of chemoattractants for haemopoietic progenitor cells by bone marrow endothelial cells: a possible role in homing of haemopoietic progenitor cells to bone marrow", British Journal of Haematology, 1999, p. 905-911, vol. 106.

Ishida et al., "Specific Recruitment of CC Chemokine Receptor 4-Positive Regulatory T Cells in Hodgkin Lymphoma Fosters Immune Privilege", Cancer Research, Jun. 1, 2006, p. 5716-5722, vol. 66, No. 11.

Ishida et al., "CCR4 as a novel molecular target for immunotherapy of cancer", Cancer Science, Nov. 2006, p. 1139-1146, vol. 97, No. 11.

Ishida et al., "CXC Chemokine Receptor 3 and CC Chemokine Receptor 4 Expression in T-Cell and NK-Cell Lymphomas with Special Reference to Clinicopathological Significance for Peripheral T-Cell Lymphoma, Unspecified", Clinical Cancer Research, 2004, p. 5494-5500, vol. 10.

Ishida et al., "The CC Chemokine Receptor 4 as a Novel Specific Molecular Target for Immunotherapy in Adult T-Cell Leukemia/Lymphoma", Clinical Cancer Research, Nov. 15, 2004, p. 7529-7539, vol. 10.

Jöhrer et al., "Up-Regulation of Functional Chemokine Receptor CCR3 in Human Renal Cell Carcinoma", Clinical Cancer Research, 2005, p. 2459-2465, vol. 11.

Kimsey et al., "Co-localization of Macrophage Inflammatory Protein-3α (Mip-3 α) and Its Receptor, CCR6, Promotes Pancreatic Cancer Cell Invasion", The Cancer Journal, Nov./Dec. 2004, p. 374-380, vol. 10, No. 6.

Kleeff et al., "Detection and Localization of MIP-3α/LARC/Exodus, a Microphage Proinflammatory Chemokine, and its CCR6 Receptor in Human Pancreatic Cancer", Int. J. Cancer, 1999, p. 650-657, vol. 81, No. 4.

Kute et al., "Development of Herceptin Resistance in Breast Cancer Cells", Cytometry Part A 57A, 2004, p. 86-93.

Letsch et al., "Functional CCR9 Expression Is Associated with Small Intestinal Metastasis", The Journal of Investigative Dermatology, 2004, p. 685-690, vol. 122.

Libura et al., "CXCR4-SDF-1 signaling is active in rhabdomyosarcoma cells and regulates locomotion, chemotaxis, and adhesion: Presented at the Annual Meeting of the American Society of Hematology in Orlando, FL, Dec. 7-11, 2001", Blood, Oct. 2002, p. 2597-2606, vol. 100, No. 7.

Mantovani et al., "Macrophage-derived chemokine (MDC)", Journal of Leukocyte Biology, Sep. 2000, p. 400-404, vol. 68.

Meijer et al., "The CXCR5 Chemokine Receptor Is Expressed by Carcinoma Cells and Promotes Growth of Colon Carcinoma in the Liver", Cancer Research, 2006, p. 9576-9582, vol. 66.

Menard et al. "Biologic and therapeutic role of HER2 in cancer", Oncogene, 2003, p. 6570-6578, vol. 22.

Müller et al., "Involvement of chemokine receptors in breast cancer metasis", Nature, Mar. 2001, p. 50-56, vol. 410.

Nagtegaal et al., "Local and distant recurrences in rectal cancer patients are predicted by the nonspecific immune response; specific immune response has only a systematic effect—a histopathological and immunohistochemical study", BMC Cancer, 2001, 11 pages, vol. 1, No. 7.

Nakamura et al., "RANKL-induced CCL22/macrophage-derived chemokine produced from osteoclasts potentially promotes the bone metastasis of lung cancer expressing its receptor CCR4", Clin Exp Metastasis, 2006, p. 9-18, vol. 23.

Nakanishi et al., "Expression of macrophage-derived chemokine (MDC)/CCL22 in human lung cancer", Cancer Immunology Immunotherapy, 2006, p. 1320-1329, vol. 55.

Nakayama et al., "Selective Induction of Th2-Attracting Chemokines CCL17 and CCL22 in Human B Cells by Latent Membrane Protein 1 of Epstein-Barr Virus", Journal of Virology, Feb. 2004, p. 1665-1674, vol. 78, No. 4.

Negus et al., "The Detection and Localization of Monocyte Chemoattractant Protein-1 (MCP-1) in Human Ovarian Cancer", J. Clin. Invest., May 1995, p. 2391-2396, vol. 95.

Pils et al., "In ovarian cancer the prognostic influence of HER2/neu is not dependent on the CXCR4/SDF-1 signalling pathway", British Journal of Cancer, 2007, p. 485-491, vol. 96.

Sallusto et al., "Distinct patterns and kinetics of chemokine production regulate dendritic cell function", Eur. J. Immunol., 1999, p. 1617-1625, vol. 29.

Salvucci et al., "The role of CXCR4 receptor expression in breast cancer: a large tissue microarray study", Breast Cancer Research and Treatment, 2006, p. 275-283, vol. 97.

Schmid et al., "CXCR4 is expressed in ductal carcinoma in situ of the breast and in atypical ductal hyperplasia", Breast Cancer Research and Treatment, 2004, p. 247-250, vol. 84.

Scotton et al., "Epithelial Cancer Cell Migration: A Role for Chemokine Receptors?", Cancer Research, Jul. 1, 2001, p. 4961-4965, vol. 61.

Scotton et al., "Multiple Actions of the Chemokine CXCL12 on Epithelial Tumor Cells in Human Ovarian Cancer", Cancer Research, Oct. 15, 2002, p. 5930-5938, vol. 62.

Senchenko et al., "Deletion mapping using quantitative real-time PCR identifies two distinct 3p21.3 regions affected in most cervical carcinomas", Oncogene, 2003, p. 2984-2992, vol. 22.

Solinas et al., "Tumor-associated macrophages (TAM) as major players of the cancer-related inflammation", Journal of Leukocyte Biology, Nov. 2009, p. 1065-1093, vol. 86.

Vestergaard et al., "A Th2 Chemokine, TARC, Produced by Keratinocytes May Recruit CLA$^+$CCR4$^+$ Lymphocytes into Lesional Atopic Dermatitis Skin", The Journal of Investigative Dermatology, Oct. 2000, p. 640-646, vol. 115, No. 4.

Woerner et al., "Widespread CXCR4 Activation in Astrocytomas Revealed by Phospho-CXCR4-Specific Antibodies", Cancer Research, 2005, p. 11392-11399, vol. 65.

Zeelenberg et al., "The Chemokine Receptor CXCR4 Is Required for Outgrowth of Colon Carcinoma Micrometastases", Cancer Research, Jul. 1, 2003, p. 3833-3839, vol. 63.

Zlotnik. "Chemokines and cancer", Intl. J. Cancer, 2006, p. 2026-2029, vol. 119.

Kanagawa et al.; "CC-chemokine ligand 17 gene therapy induces tumor regression through augmentation of tumor-infiltrating immune cells in a murine model of preexisting CT26 colon carcinoma"; Int. J. Cancer; 121:2013-2022 (2007).

Slettenaar et al.; "Chemokine expression profiles of normal and malignant human cervical epithelium"; *Proc. Amer. Assoc. Cancer Res.*; vol. 46, abstract No. 4695 (2005).

Slettenaar et al. "CCR4 expression by malignant human cervical epithelial cells and tumour associated macrophages"; Poster session presented at: 97th Annual American Association for Cancer Research; Apr. 1-5, 2006, Washington, D.C.

Slettenaar, Violet I.F. "The Chemokine Network and Infiltrating Leukocytes in Cervical Cancer"; Doctoral Thesis for Queen Mary, University of London. 246 pages. Catalogued Apr. 4, 2007, Senate House Library.

Wagsaeter et al.; "Quantification of the chemokines CCL17 and CCL22 in human colorectal adenocarcinomas"; *Mol. Med. Reports*; 1:211-217 (2008).

(56) References Cited

OTHER PUBLICATIONS

Weihrauch et al.; "Elevated Serum Levels of CC Thymus and Activation-Related Chemokine (TARC) in Primary Hodgkin's Disease: Potential for a Prognositc Factor"; *Cancer Res*.; 65:5516-5519 (2005) *ePub* Jul. 1, 2005.

"Tangible Material: HT-29: Human Colorectal Adenocarcinoma Cell Line," Memorial Sloan Kettering Cancer Center, downloaded on Feb. 26, 2014 from http://www.mskcc.org/research/technology/human-coloretal-adenocarcinoma-cell-line-ht-29.

Beaulieu et al., "Clonal Analysis of Sucrase-Isomaltase Expression in the Human Colon Adenocarcinoma Caco-2 Cells," The Biochemical Journal 280: 599-608 (1991).

Dwinell et al., "Chemokine Receptor Expression by Human Intestinal Epithelial Cells," Gastroenterology 117(2): 359-367 (1999).

\* cited by examiner

Figure 8

Panel A: Positivity / Percentage of cells

| Stage | n= | +0 (0) | +1 (0-10) | +2 (10-20) | +3 (21-30) | +4 (>30) |
|---|---|---|---|---|---|---|
| Normal | 23 | 13.00% (3/23) | 86.96% (20/23) | 0 | 0 | 0 |
| CIN I | 30 | 3.33% (1/30) | 40.00% (12/30) | 43.33% (13/30) | 10.00% (3/30) | 3.33% (1/30) |
| CIN II | 17 | 5.88% (1/17) | 41.18% (7/17) | 41.18% (7/17) | 5.88% (1/17) | 5.88% (1/17) |
| CIN III | 14 | 0 | 50.00% (7/14) | 42.86% (6/14) | 0 | 7.14% (1/14) |
| SCC | 41 | 2.44% (2/41) | 14.63% (6/41) | 41.46% (17/41) | 31.71% (13/14) | 9.76% (4/41) |
| RECUR. | 15 | 0 | 53.33% (8/15) | 26.67% (4/15) | 13.33% (2/15) | 6.67% (1/15) |
| LN METS | 10 | 0 | 10.00% (1/10) | 30.00% (3/10) | 50.00% (5/10) | 10.00% (1/10) |
| ADENOCA | 10 | 10.00% (1/10) | 60.00% (6/10) | 30.00% (3/10) | 0 | 0 |

Panel B: Staining intensity

| Stage | n= | 0 (none) | 1 (+) | 2 (++) | 3 (+++) |
|---|---|---|---|---|---|
| Normal | 23 | 13.04% (3/23) | 52.17 (12/23) | 21.73% (5/23) | 13.04% (3/23) |
| CIN I | 30 | 3.33% (1/30) | 6.66% (2/30) | 50.00% (15/30) | 40.00% (12/30) |
| CIN II | 17 | 5.88% (1/17) | 17.65 (3/17) | 47.05% (8/17) | 29.41% (5/17) |
| CIN III | 14 | 0 | 21.43% (3/14) | 42.86% (6/14) | 35.71% (5/14) |
| SCC | 41 | 2.43% (1/41) | 7.31% (3/41) | 34.15% (14/41) | 56.10% (23/41) |
| RECUR. | 15 | 0 | 13.33% (2/15) | 33.33% (5/15) | 53.33% (8/15) |
| LN METS | 10 | 0 | 0 | 20.00% (2/10) | 80.00% (8/10) |
| ADENOCA | 10 | 10.00% (1/10) | 20.00% (2/10) | 50.00% (5/10) | 20.00% (2/10) |

Figure 9

Panel A: Positivity / Percentage of cells

| Stage | n= | +0 (0%) | +1 (<25%) | +2 (26-50%) | +3 (51-75%) | +4 (>76%) |
|---|---|---|---|---|---|---|
| Normal | 23 | 95.65% (22/23) | 0 | 4.34% (1/23) | 0 | 0 |
| CIN I | 30 | 3.33% (1/30) | 13.33% (4/30) | 16.66% (5/30) | 6.66% (2/30) | 60.00% (18/30) |
| CIN II | 17 | 5.88% (1/17) | 11.76% (2/17) | 5.88% (1/17) | 17.75% (3/17) | 58.82% (10/17) |
| CIN III | 16 | 6.25% (1/16) | 6.25% (1/16) | 12.50% (2/16) | 25.00% (4/16) | 50.00% (8/16) |
| SCC | 45 | 4.44% (2/45) | 2.22% (2/45) | 0 | 11.11% (5/45) | 82.22% (37/45) |
| RECUR. | 15 | 0 | 6.67% (1/15) | 13.33% (2/15) | 0 | 80.00% (12/15) |
| LN METS | 10 | 0 | 10.00% (1/10) | 0 | 20.00% (2/10) | 70.00% (7/10) |
| ADENOCA | 10 | 10.00% (1/10) | 10.00% (1/10) | 20.00% (2/10) | 20.00% (2/10) | 40.00% (4/10) |

Panel B: Staining intensity

| Stage | n= | 0 (none) | 1 (+) | 2 (++) | 3 (+++) |
|---|---|---|---|---|---|
| Normal | 23 | 95.65% (22/23) | 4.34% (1/20) | 0 | 0 |
| CIN I | 30 | 3.33% (1/30) | 16.66% (5/30) | 30.00% (9/30) | 50.00% (15/30) |
| CIN II | 17 | 5.88% (1/17) | 29.41% (5/17) | 35.29% (6/17) | 29.41% (5/17) |
| CIN III | 16 | 6.25% (1/16) | 25.00% (4/16) | 50.00% (8/16) | 18.75% (3/16) |
| SCC | 45 | 4.44% (2/45) | 22.22% (10/45) | 37.78% (17/45) | 35.56% (16/45) |
| RECUR. | 15 | 0 | 26.66% (4/15) | 26.66% (4/15) | 46.67% (7/15) |
| LN METS | 10 | 0 | 40.00% (4/10) | 20.00% (2/10) | 40.00% (4/10) |
| ADENOCA | 10 | 10.00% (1/10) | 30.00% (3/10) | 30.00% (3/10) | 30.00% (3/10) |

Figure 13

```
<400>  1
atgaacccca cggatatagc agataccacc ctcgatgaaa gcatatacag caattactat        60
ctgtatgaaa gtatccccaa gccttgcacc aaagaaggca tcaaggcatt tggggagctc       120
ttcctgcccc cactgtattc cttggttttt gtatttggtc tgcttggaaa ttctgtggtg       180
gttctggtcc tgttcaaata caagcggctc aggtccatga ctgatgtgta cctgctcaac       240
cttgccatct cggatctgct cttcgtgttt tccctccctt tttggggcta ctatgcagca       300
gaccagtggg ttttggggct aggtctgtgc aagatgattt cctggatgta cttggtgggc       360
ttttacagtg gcatattctt tgtcatgctc atgagcattg atagatacct ggcgatagtg       420
cacgcggtgt tttccttgag ggcaaggacc ttgacttatg gggtcatcac cagtttggct       480
acatggtcag tggctgtgtt cgcctccctt cctggctttc tgttcagcac ttgttatact       540
gagcgcaacc atacctactg caaaaccaag tactctctca actccacgac gtggaaggtt       600
ctcagctccc tggaaatcaa cattctcgga ttggtgatcc ccttagggat catgctgttt       660
tgctactcca tgatcatcag gaccttgcag cattgtaaaa atgagaagaa gaacaaggcg       720
gtgaagatga tctttgccgt ggtggtcctc ttccttgggt ctgacacctt tacaacata       780 gtgctcttcc tagagaccct ggtggagcta gaagtccttc aggactgcac ctttgaaaga       840
tacttggact atgccatcca ggccacagaa actctggctt tgttcactg ctgccttaat       900 cccatcatct actttttct ggggagaaa tttcgcaagt acatcctaca gctcttcaaa       960
acctgcaggg ccttttgt gctctgccaa tactgtgggc tcctccaaat ttactctgct      1020 gacacccca gctcatctta cacgcagtcc accatggatc atgatcttca tgatgctctg      1080
tag                                                                   1083
```

CANCER MARKER AND THERAPEUTIC TARGET

REFERENCE TO A SEQUENCE LISTING

This application includes a sequence listing in a text file entitled 028385-000100_ST25.txt, created on Jun. 25, 2010, and containing 5 kilobytes. The material contained in the text file is hereby incorporated by reference.

FIELD OF THE INVENTION

The invention relates to oncology and methods of cancer diagnosis, stratification, disease staging and treatment. The field of the invention therefore concerns markers of predictive or clinical value in cancer diagnosis and treatment and the use of medicaments for the treatment of cancer. The invention also concerns screening assays for identifying active anticancer agents.

BACKGROUND TO THE INVENTION

Chemokine receptors and their ligands direct the trafficking of cells in normal tissue homeostasis and in disease, influencing cell motility, invasiveness and survival [1]. In inflammation and in cancer, chemokines in the diseased tissues contribute to the rolling, tethering and invasion of leucocytes from the blood vessels through the endothelial cell basement membrane and into the parenchyma [2].

CCR4 is one of 18 known chemokine receptors. Chemokine receptors are generally expressed on immune cells and in the tumour microenvironment a number of receptors and their ligands are present in the immune cell infiltrate.

In many cancers, malignant cells also express certain chemokine receptors, receptors that are not usually found on their normal counterparts. Metastatic cancer cells are thought to gain characteristics of chemokine receptor-expressing leucocytes, using chemokines to aid their migration to, and survival at, sites distant to the original tumour [3, 4, 5]. Inappropriate presence on cancer cells of chemokine receptors that usually have a highly restricted pattern of expression further supports the hypothesis that specific chemokine receptors may help cells spread to, and/or survive in, different metastatic sites [8]. In carcinomas, melanomas and haematological malignancies, expression of chemokine receptors, especially CXCR4 and CCR7, on malignant cells in advanced disease, correlates with increased lymph node metastasis, greater dissemination of disease, lower disease-free survival and/or overall survival [6,7,8]. CXCR5 is normally restricted to B cells and some T cell subtypes, but is also expressed by pancreatic cancer cells where it is implicated in the establishment of liver metastases; the liver being a site of production of the CXCR5 ligand, CXCL13 [9]. Melanoma cells that have metastasised to the intestine express CCR9 [10]. In homeostasis, the CCR9 ligand CCL25 recruits rare T cell subsets to the intestine. In pancreatic cancer, expression of CCR6 has been observed [38][39]. CCR6 expression has also been reported in human renal carcinoma, together with CCR3 and CXCR2 [40].

This demonstrates that a few chemokine receptors are known to be upregulated in tumour epithelial cells in late stage carcinogenesis, including CXCR4, and are thought to play a role in invasion and metastasis. In contrast, CCR4 has only previously been reported to be upregulated in some blood cancers, particularly T cell lymphomas.

As described above, CXCR4 is commonly found on malignant cells in many advanced human cancers. In addition, Woerner et al found that CXCR4 was also present in the early stages of disease in glioblastoma [20]. However, using a phospho-specific anti-CXCR4 antibody, they found that in the less malignant Grade 1 lesions, the level of receptor activation was much lower.

Although it is generally reported that malignant cell chemokine receptor expression is associated with advanced disease, there are also a few other reports in the art of expression of a chemokine receptor on malignant cells at early and pre-invasive stages of cancer, but all of these concern CXCR4. In a large tissue array study (over 2000 samples) of breast cancer, cytoplasmic/membrane expression of CXCR4 expression was reported in 67% of ductal carcinomas in situ, DCIS [21]. This was confirmed in a study from Schmid et al who showed that both CXCR4 and its ligand CXCL12 were expressed in DCIS [22]. The inventors have also found CXCR4 on the epithelial cells of borderline non-invasive ovarian cancer tumours (Kulbe et al., manuscript in preparation) and this has also been reported by Pils et al [23].

No data on expression of other chemokine receptors on epithelial cells in early cancers is available, but there is evidence that oncogenic pathways can induce chemokine receptor expression on epithelial cells. The RET/PTC1 oncogene is necessary and sufficient for malignant transformation of primary thyrocytes [24]. This oncogene induces a pro-inflammatory programme in the thyrocytes that includes induction of functional CXCR4. Alveolar rhabdomyosarcoma is a highly aggressive tumour characterised by recurrent PAX3 and PAX7-FKHR gene fusions. Transfer of PAX3-FKHR into embryonal rhabdomyosarcoma cells also activates CXCR4 expression [Libura, 2002 #9346].

In all these studies a conclusion is that acquisition of certain chemokine receptors by malignant cells appears to be, a relatively late event in malignant progression, and in the case of CCR4, expression has not been reported at any stage of solid tumour development CCR4 expression is generally restricted to the immune system, and is known as a marker of Th2 and regulatory T cells. In the tumour environment, these cells act to suppress cytotoxic T cells and dendritic cell maturation, hence suppressing anti-tumour immune responses. In addition, CCR4 has been shown to be expressed in haematological malignancies, including by a high proportion of adult T cell lymphomas (ATL), and was a significant prognostic factor associated with metastasis to skin [35], [41]. As such, CCR4 is of interest as a therapeutic target in ATL [37], [42]. CCR4 expression by adult T cell leukaemia is associated with skin metastases; its ligands CCL17 and CCL22 are produced by both malignant cells and the skin tumor microenvironment [36]. Ishida et al have developed an anti-CCR4 monoclonal antibody therapeutic for the treatment of adult T cell lymphoma that induces ADCC activity against the tumor cells and may also act on immunosuppressive malignant Treg cells found in this disease [37].

The only report in the academic literature of a CCR4 positive solid tumor cell line is the human lung cancer cell line SBC-5 [34]. These cells migrated towards CCL22 gradients and in bone metastatic SBC-5 xenografts there was close co-localisation of osteoclasts expressing CCL22 and SBC-5 cells expressing CCR4. There are no reports of CCR4 expression in primary human tumour cells.

WO05106471 (BAYER HEALTHCARE AG) discloses screening methods for agents of potential use in treating a wide range of diseases; specifically consisting of cardiovascular disorders, gastrointestinal and liver diseases, inflammatory diseases, metabolic diseases, haematological disorders, cancer disorders, neurological disorders, respiratory diseases and reproduction disorders in a mammal. The screening method determines the degree of binding or otherwise of candidate agents to CCR4. There is also a description of the screening of a wide range of human cells and tissues for their expression level of CCR4 relative to housekeeping gene expression. The cells and tissues were obtained from disparate sources and just an isolated few were cancerous cells/tissues; e.g. thyroid, ileum, HeLa, Jurkat, lung and breast cancer cells. The results for the relative expression of CCR4 show no distinguishable pattern associated with any particular disease. Indeed amongst tumour cells tested, e.g. thyroid and ileum, there were low levels of relative expression of CCR4 and other non-tumour cells showed higher levels of relative expression of CCR4.

WO9623068 (GLAXO GROUP LIMITED) discloses a chemokine receptor able to bind to Monocyte Chemotactic Protein-1 (MCP-1/CCL2), Macrophage Inflammatory Protein 1α (MIP1α/CCL3) and/or 'RANTES' (Regulated upon Activation, Normal T-cell Expressed, and Secreted/CCL5). A nucleotide and an amino-acid sequence for CCR4 are disclosed (CC-CKR-4/K5.5. K5.5 and CC-CKR-4 are alternative names for CCR4.) The expression of CCR4 is discovered in a relatively limited range of normal human tissues and in a range of T-cell samples. There is also general disclosure of screening assays for agents capable of activating T-lymphocytes or blocking binding of ligands MCP-1, MIP-1α and/or RANTES to the chemokine receptor. There is some suggestion that active agents obtained via screening may be useful in the treatment of allergies, for example.

WO0041724A1 (LELAND STANFORD/LEUKOSITE) proposes the modulation of systemic memory T cell trafficking by administration of CCR4 modulating agents. This is intended as a treatment for inflammatory skin disease. Substances capable of modulating CCR4 binding to its ligands are used in in vitro tests to show how T-cell migration is affected.

Antibodies reactive against CCR4 are known. WO0164754 (Kyowa Hakko Kogyo) discloses a recombinant antibody or fragment thereof allegedly reactive specifically with the extracellular domain of CCR4. Also disclosed is a polypeptide sequence of such an antibody. There is also disclosed an antibody which reacts with a CCR4 positive cell and is cytotoxic or causes antibody-dependent cell-mediated cytotoxicity (ADCC.) These antibodies are proposed for the use in the treatment of Th2-mediated immune diseases or blood cancer, specifically leukaemia.

WO05035582 (Kyowa Hakko Kogyo) discloses an antibody capable of specifically binding CCR4 and also discloses a CCR4 antibody which has a complex N-linked glycosylation in the Fc region. Also disclosed are antibodies to the extracellular domains of CCR4.

WO03018635 (Kyowa Hakko Kogyo) discloses 'Human CDR-grafted antibodies and fragments'. A specific CDR (complementarity determining region) which binds specifically to CCR4 is disclosed. The antibodies are proposed for use in the diagnosis or treatment of Th2-mediated immune diseases or cancers such as blood cancers.

WO05053741 (Kyowa Hakko Kogyo) discloses a medicament comprising a recombinant antibody, which specifically binds CCR4, in combination with at least one other agent. The antibody is proposed for the treatment of tumours, specifically haematopoietic organ tumours.

WO0042074 (MILLENIUM PHARMACEUTICALS) discloses antibodies to CCR4 and antibodies that can compete with their binding. No specific diagnostic applications are disclosed. Therapy of inflammatory disorders is proposed.

Also known in the art are a variety of small molecules that bind to the CCR4 receptor.

WO04007472 (ONO PHARMACEUTICAL CO.) discloses a small molecule tricyclic compound with anti-CCR4 activity.

WO05023771 (ONO PHARMACEUTICAL CO.) discloses small molecule nitrogen-containing heterocyclic compounds with anti-CCR4 activity.

WO02094264 (TULARIK INC.) discloses specific compounds with CCR4 inhibitory activities.

WO0230358 (TULARIK/CHEMOCENTRYX) discloses various CCR4-binding compounds and uses for treatment of various diseases, but not including cancer.

WO0230357 (CHEMOCENTRYX) discloses compounds that are antagonists of CCR4. This application describes uses for the treatment of inflammatory diseases and conditions.

WO051236976 (ASTELLAS PHARMA INC.) discloses quinazoline derivatives as CCR4 regulators.

WO05085212 (YAMANOUCHI PHARMACEUTICAL CO., LTD.) discloses pyrimidine derivatives as CCR4 modulators.

WO05082865 (YAMANOUCHI PHARMACEUTICAL CO., LTD.) discloses fused bicyclic pyrimidine derivatives as CCR4 function-controlling agents.

WO04108717 (ASTRAZENECA AB) discloses sulphonamide compounds that modulate chemokine (specifically CCR4) receptor activity.

EP1633729 (ASTRAZENECA AB) discloses sulphonamide compounds that modulate chemokine (specifically CCR4) receptor activity.

WO03014153 (TOPIGEN PHARMACEUTIQUE INC.) discloses another technology in the art, a method of modulating viral infection of a cell by modulating the interaction between chemokine receptors (including CCR4) and a virus.

WO2004/045526 (Morehouse School of Medicine) discloses antibodies to particular chemokines and chemokine receptors and their use in inhibiting the growth and metastasis of cancer cells. Antibodies were raised against the particular chemokine receptors and their ligands, which does not include CCR4. Also described are methods of testing for over-expression of particular chemokines in a tumour and the suggestion that such tumours can be treated by administering antibodies against the particular over-expressed chemokine or chemokine receptor.

WO99/15666 (Icos Corporation) discloses nucleotide sequences and polypeptide sequences of a macrophage-derived C-C chemokine designated 'Macrophage Derived Chemokine' (MDC). MDC appears synonymous with CCL22. TARC appears synonymous with CCL17. Methods for the recombinant or synthetic production of MDC protein or polypeptide fragments are described. Also disclosed are antibodies reactive with MDC as well as assays for identifying modulators of MDC and TARC chemokine activity.

Cervical cancer is the second most common type of cancer in women worldwide. Symptoms are often absent until the cancer is at a late stage and hence cervical cancer has been the subject of an intense population screening program using the Pap smear, which can detect pre-malignant changes by histopathology. Although an abnormal Pap smear indicates possible cervical neoplasia, it is insufficient for diagnosis, which is subsequently carried out by biopsy and additional invasive procedures ('colposcopy'). In total, 24,000 women are referred in the UK each year with abnormal Pap smears. The Pap smear has only 70% sensitivity, hence a significant proportion of women with cervical cancer or pre-invasive lesions remain undiagnosed. Therefore, more accurate screening methods are required to i) allow screening to be more automated and less subjective ii) to improve the sensitivity of screening.

HPV (Human Papilloma Virus) infection is found in the majority of invasive cervical carcinomas, one strategy is to screen for the presence of HPV markers such as E6 and E7 in concert with the Pap smear. However, due to the high level of HPV infection in the sexually active population (up to 80% infection history), this also results in the identification of a large number of false positives and makes the accuracy of the test dependent on HPV prevalence. As such, identifying new biomarkers for cervical cancer remains an area of active interest.

Furthermore new or alternative biomarkers are required for other forms of cancer including, but not limited to, the following cancer types: bronchial, nasopharyngeal, laryngeal, small cell and non-small cell lung, skin (e.g. melanoma or basal cell carcinoma), brain, pancreatic, neck, lung, kidney, liver, breast, colon, bladder, oesophagus, stomach, cervical, ovarian, germ cell and prostate. A biomarker characteristic of one cancer type may be shared with other cancer types thus the use of a biomarker may extend beyond the original cancer type it was found to be associated with.

There is a need for improved biomarkers for a range of cancers which allow for stratification of patients in need of anti-cancer treatment.

The stage of a cancer is a descriptor (usually numbers I to IV) of how much the cancer has spread. The stage often takes into account the size of a tumour, how deep it has penetrated, whether it has invaded adjacent organs, if and how many lymph nodes it has metastasized to, and whether it has spread to distant organs. Staging of cancer is important because the stage at diagnosis is the most powerful predictor of survival, and treatments are often changed based on the stage Correct staging is critical because treatment is directly related to disease stage. Thus, incorrect staging would lead to improper treatment, and material diminution of patient survivability. Correct staging, however, can be difficult to achieve. Pathologic staging, where a pathologist examines sections of tissue, can be particularly problematic for two specific reasons: visual discretion and random sampling of tissue. "Visual discretion" means being able to identify single cancerous cells intermixed with healthy cells on a slide. Oversight of one cell can mean mis-staging and lead to serious, unexpected spread of cancer. "Random sampling" refers to the fact that samples are chosen at random from patients' lymph nodes and are examined. If cancerous cells present in the lymph node happen not to be present in the slices of tissue viewed, incorrect staging and improper treatment can result.

There is an ongoing need for new treatments against cancer, whether these involve improved ways of administering existing anti-cancer agents, or whether these involve identifying, testing and verifying effective new anti-cancer agents. There is also an ongoing need for improved methods of monitoring the efficacy of existing and any new anti-cancer agents in the course of a given treatment regime. Improved methods of generating data of predictive value are needed. The dosage and frequency of treatments using anti-cancer agents is an important factor. Also, the timing of the start of an anti-cancer treatment relative to the stage of progression of a cancer, or relative to a patient group, are important factors. Improved methods of monitoring are required in order to seek optimal treatments for patients, whether as individuals or classified into groups by virtue of genetic, phenotypic or other characteristics.

An example of the prognostic function of a biomarker in the choice of treatment for a patient is the use of the anti-cancer drug Herceptin (Trastumuzab). The HER2/neu gene is a proto-oncogene located at the long arm of human chromosome 17(17q11.2-q12) and amplification of HER2/neu occurs in 25-30% of early-stage breast cancers. In cancer the growth promoting signals from HER2/neu are constitutively transmitted, promoting invasion, survival and angiogenesis of cells. Furthermore overexpression can also confer therapeutic resistance to cancer therapies. Herceptin (Trastumuzab) is a humanised monoclonal antibody which binds to the extracellular segment of the receptor HER2/neu, (also known as ErbB-2) and is only effective in treating breast cancer where the HER2/neu receptor is overexpressed. Because of its prognostic role as well as its ability to predict a patient's response to Herceptin breast tumors are routinely checked for overexpression of HER2/neu by a variety of techniques including immunohistochemistry (IHC) Chromogenic and fluorescence in situ hybridisation (CISH and FISH respectively).

There also exists the need for more accurate and reliable methods of diagnosing/staging of cancers and a need for new methods for screening anti-cancer agents.

SUMMARY OF THE INVENTION

The inventors have surprisingly discovered that in certain solid tumours, chemokine receptor CCR4 expression is an early event in carcinogenesis. In addition the inventors have discovered that the expression of two ligands of CCR4, CCL17 and CCL22, increases during tumour progression.

The present invention provides a method of obtaining information of predictive or diagnostic character for a cancer patient, comprising the step of measuring the amount and/or activity of chemokine receptor CCR4 expressed by tumour cells in a solid tumour sample or in a non-haematological cell tumour sample taken from the patient, the amount and/or activity of CCR4 providing the information of predictive or diagnostic character.

Haematological tumours are derived from blood cells, including immune cells and include leukaemias and lymphomas of various types. The invention does not therefore concern haematological tumours.

In the solid or non-haematological tumours which the invention is concerned with, CCR4 is expressed by cells of the tumour. The methods of the invention therefore concern the CCR4 expressed by samples of patient tumour cells (or reference cells) and substantially not by cells of the immune system. To the extent that CCR4 arises in any patent tumour samples from an undesired source, such as infiltrating immune cells, the amount and/or activity of CCR4 being measured in accordance with the invention is either not significant or it is controlled for in any measurements being made.

In preferred embodiments, the reference amount and/or level of activity of CCR4 may be measured in one or more non-tumour samples. The, or at least one non-tumour sample may be taken from the patient. When a reference amount and/or level of activity of CCR4 is determined from non-tumour cells of the patient, a single sample of non-tumour tissue may be taken from the patient. If desired, a multiplicity of non-tumour samples can be taken from different locations of the same patient. The reference amount may therefore be a mean figure determined from a number of samples taken from the patient.

In other embodiments, the one or more non-tumour samples are optionally not taken from the patient. Such samples may be taken from other patients and may include cultured tumour cell lines.

The information may be used to predict whether the solid tumour or the non-haematological cell tumour of the patient will be susceptible to an anti-cancer treatment. This aspect of the invention advantageously permits stratification of cancer patients. This allows an optimal anti-cancer treatment or regime to be identified for a given individual patient.

In preferred embodiments, the patient will have received an anti-cancer treatment and measurements of the amount and/or activity of CCR4 in the solid tumour sample or the non-haematological tumour sample of the patient may be made before and after the start of treatment, and the information obtained is then used to determine whether the solid tumour or the non-haematological cell tumour of the patient has responded to the anti-cancer treatment. This aspect of the invention advantageously permits monitoring of cancer patients to determine how their individual treatment is progressing. Adjustments to the treatment regime may be made in light of the progress being made.

The information may be used in diagnosis of a solid tumour or a non-haematological cell tumour.

The information may be used to stage a solid tumour or a non-haematological cell tumour.

The invention also provides a method of obtaining information of predictive or diagnostic character for a cancer patient whose tumour cells express chemokine receptor CCR4, comprising the step of measuring the amount and/or activity of CCR4 ligand CCL17 and/or CCL22 in a solid tumour sample or in a non-haematological cell tumour sample taken from the patient, the amount and/or activity of CCL17 and/or CCL22 providing the information of predictive or diagnostic character.

The information of predictive or diagnostic character may be obtained by comparing the amount and/or activity of CCL17 and/or CCL22 in the solid tumour sample or in the non-haematological cell tumour sample with a reference amount and/or level of activity of CCL17 and/or CCL22.

The reference amount and/or level of activity of CCL17 and/or CCL22 may be measured in one or more non-tumour samples. As in the previous aspect of the invention, non-tumour samples may be taken from the patient or from a different patient or source, including cultured cell lines.

The information may be used to predict whether the solid tumour or the non-haematological cell tumour of the patient will be susceptible to an anti-cancer treatment.

In further optional embodiments, the patient has received an anti-cancer treatment and measurements of the amount and/or activity of CCL17 and or CCL22 are made before and after the start of treatment and the information obtained is used to determine whether the solid tumour or the non-haematological cell tumour of the patient has responded to the anti-cancer treatment.

In all aspects of the invention, a particular anti-cancer treatment may comprise an agent which modulates or inhibits CCR4 expression or activity.

The invention also provides the use of an antibody reactive against chemokine receptor CCR4 for detecting the presence or measuring the amount of CCR4 expressed by a solid tumour or a non-haematological tumour in a cancer patient, the presence or amount of CCR4 expressed by the tumour and when detected or measured providing the information of diagnostic character.

The invention further provides the use of an oligonucleotide primer or probe capable of hybridizing under stringent conditions to a nucleic acid of SEQ ID NO:1 for detecting or measuring the amount of expression of CCR4 by cells of a solid tumour or a non-haematological tumour, the presence or amount of CCR4 expressed by the tumour when detected or measured providing the information of diagnostic character.

The aforementioned uses to which the information may be put are as hereinbefore defined in relation to the method aspects of the invention.

The nucleic acid of SEQ ID NO:1 is not limited to the specific sequence, but includes variants which still encode biologically active CCR4 protein. Such variants may include nucleotide sequences having at least 99% identity with SEQ ID NO:1. Other variants may have at least 95%, optionally at least 90% identity. The range of identities of from at least 65% to at least 99% identity with SEQ ID NO:1 is disclosed herein.

A variety of stringent hybridisation conditions will be familiar to the skilled reader in the field. Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences that Share at Least 90% Identity to Hybridize)

| | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |

High Stringency (Allows Sequences that Share at Least 80% Hybridize)

| | |
|---|---|
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |

Low Stringency (Allows Sequences that Share at Least 50% Identity to Hybridize)

| | |
|---|---|
| Hybridization: | 6x SSC at RT to 55° C. for 16-20 hours |
| Wash at least twice: | 2x-3x SSC at RT to 55° C. for 20-30 minutes each. |

The invention includes a method of treating a cancer patient having a solid tumour or a non-haematological tumour expressing CCR4, comprising administering an effective amount of an agent which modulates or inhibits CCR4 expression or activity.

The agent may be administered in the form of a pharmaceutical formulation. Suitable formulations include sterile aqueous or non-aqueous solutions, suspensions, and emulsions. The compositions may further comprise auxiliary agents or excipients, as known in the art, see, e.g., Berkow et al., The Merck Manual, 16th edition Merck & Co., Rahman, N.J. (1992), Avery's Drug_Treatment: Principles and Practice of Clinical Pharmacology and Therapeutics, 3rd edition, ADIS Press, Ltd., Williams and Wilkins, Baltimore, Md. (1987) & Osol (ed.), Remington's Pharmaceutical Sciences, Mack Publishing Co., Easton, Pa. 1324-1341 (1980). The pharmaceutical compositions administered in accordance with the invention are preferably presented in the form of individual doses (unit doses).

A composition or medicament employed in the methods and uses of the invention may further comprise salts, buffers, or other substances which are desirable for improving the efficacy of the composition. The administration of composition or medicament in accordance with the invention may be local or systemic.

The invention also includes the use of a chemokine receptor CCR4 modulating or inhibiting agent for the treatment or prevention of solid tumours or non-haematological tumours.

In all of the aforementioned method and use aspects of the invention, the agent which modulates or inhibits CCR4 expression or activity may be:
  (i) an antibody which binds to CCR4; optionally an anti-CCR4 antibody as disclosed in any of WO0041724, WO0164754, WO05035582, WO03018635, WO05053741, WO0042074; or
  (ii) an antibody which binds to CCR4 ligands CCL17 or CCL22; optionally anti-CCL17 or anti-CCL22 antibodies as disclosed in WO99/15666 or Ishida, T., et al (2004) Clin Cancer Res 10:7529-7539.
  (iii) a CCR4 antagonist; optionally a CCR4 antagonist as disclosed in any of WO04007472, WO05023771, WO02094264, WO0230358, WO0230357, WO051236976, WO05085212, WO05082865, WO04108717, EP1633729, WO03014153.

Appropriate compositions and formulations of active agents include those described in the aforementioned publications.

The invention further provides a kit for obtaining information of predictive or diagnostic character for a cancer patient from a solid tumour or a non-haematological tumour sample from the patient, wherein the kit comprises:
  at least one reagent selected from an antibody reactive with CCR4, an antibody reactive with CCL17, an antibody reactive with CCL22, and an oligonucleotide probe or primer capable of hybridizing with SEQ ID NO:1 under stringent conditions; and
  indicia directing a user of the kit to apply the reagent to a sample of a solid tumour or a non-haematological tumour from a patient so as to measure the amount and/or activity of one or more of CCR4, CCL17 and CCL22 in the sample.

In certain embodiments, the kit may comprise a reference sample of one or more non-tumour cells and the indicia are a set of instructions and direct the user of the kit to measure the amount and/or level of activity of one or more of CCR4, CCL17 and CCL22 in both the patient sample and the reference sample. The reference sample(s) may comprise cultured tumour cell or cell extracts.

In other embodiments, the indicia may be a set of instructions and include reference values for the reference amount and/or level of activity of one or more of CCR4, CCL17 and CCL22. The reference values are preferably obtained by previous work carried out by making measurements of amounts and/or activity of CCR4, CCL17 or CCL22 in selected non-tumour samples from individuals or patients, whether or not they have or have had a cancerous condition. Such previous measurements may have been carried out on cultured non-tumour human cell lines.

The invention also includes a method of screening for an anti-cancer agent active against a solid tumour or a non-hematological tumour which expresses chemokine receptor CCR4 comprising the steps of:
  i) providing test cells that express CCR4 and are capable of, or are in the process of exhibiting a biological activity selected from (a) proliferation, (b) migration, (c) secretion of a protein or a signalling molecule, or (d) cell survival when cultured under specified conditions;
  ii) exposing the test cells to a candidate agent for a period of time,
  iii) measuring the biological activity of the test cells, whereby no biological activity or biological activity which is less than the expected activity of such test cells in the absence of candidate agent identifies an anti-cancer agent.

In preferred methods, a control aliquot of test cells is not exposed to the candidate agent and the biological activity of the control cells is measured so that the expected biological activity is determined.

The biological activity of the test cells and any control cells may be induced by the addition of a ligand of the CCR4 receptor, preferably CCL17 and/or CCL22.

In all aspects of the invention, the solid tumour or non-haematological tumour may be a cancer selected from cancer of the cervix, oesophagus, kidney, brain, breast, ovary, prostate, stomach or pancreas. The invention may be of particular advantage in relation to cancers of the cervix, oesophagus, kidney, brain, breast and ovary.

The invention therefore provides a method for determining whether a cancer patient is suitable for treatment with an agent that modulates CCR4 expression and/or CCR4 activity, comprising determining the amount or activity of CCR4 in a sample of patient tumour cells.

The invention further provides a method for determining whether a cancer patient is suitable for treatment with an agent that modulates the levels or activity of CCL17 and/or CCL22, comprising determining the amount or activity of CCL17 and/or CCL22 in a sample of patient tumour cells.

The invention therefore provides for the use CCR4, CCL17, and/or CCL22 as a biomarker for stratification of cancer patients according to their suitability for treatment with CCR4, CCL17 and/or CCL22 modulating or inhibiting agents, including the agents disclosed herein.

The suitability of a cancer patient for treatment with a particular therapeutic agent is governed by a multiplicity of factors, some inter-related. Patient age, sex, stage of the cancer, type of cancer, genetic make up of patient, lifestyle factors, such at diet or smoking, may all impact on the potential outcome of a given treatment regime. Stratification is usually undertaken in order to group patients on the basis of a multiplicity of selected parameters that can allow predictions to be made in terms of clinical outcome for a group of patients or an individual patient falling within a group.

Generally, an increased level or activity of one or more of CCR4, CCL17 and/or CCL22 in a patient tumour sample is indicative of a patient for whom treatment with the anti-cancer agents disclosed herein is beneficial.

The invention also includes a method of monitoring the efficiency of an anti-cancer treatment in a patient comprising determining the amount or activity of CCR4 in a sample of tumour cells from the patient, The invention further includes a method of monitoring the efficiency of an anti-cancer treatment in a patient comprising determining the amount or activity of CCL17 and/or CCL22 in a sample of tumour cells from the patient.

In the aforementioned methods, the sampling of tumour cells may take place before, during and/or subsequent to the anti-cancer agent being administered.

The invention also provides methods for prevention or treatment of certain solid tumours as described herein comprising administration of an agent selected from:
(a) CCR4 modulating agents e.g. as disclosed in WO0041724A1 (LELAND STANFORD/LEUKO-SITE);
(b) anti-CCR4 antibodies, e.g. as disclosed in WO0164754 (Kyowa Hakko Kogyo), WO05035582 (Kyowa Hakko Kogyo), WO03018635 (Kyowa Hakko Kogyo), WO05053741 (Kyowa Hakko Kogyo) or WO0042074 (MILLENIUM PHARMACEUTICALS); or
(c) CCR4 antagonists, e.g. as disclosed in WO04007472 (ONO PHARMACEUTICAL CO.), WO05023771 (ONO PHARMACEUTICAL CO.), WO02094264 (TULARIK INC.), WO0230358 (TULARIK/CHEMOCENTRYX), WO0230357 (CHEMOCENTRYX), WO051236976 (ASTELLAS PHARMA INC.), WO05085212 (YAMANOUCHI PHARMACEUTICAL CO., LTD.), WO05082865 (YAMANOUCHI PHARMACEUTICAL CO., LTD.), WO04108717 (ASTRAZENECA AB), EP1633729 (ASTRAZENECA AB) or WO03014153 (TOPIGEN PHARMACEUTIQUE INC.)

The invention therefore also provides a method for diagnosing a solid tumour in an individual susceptible to treatment with CCR4 modulating agents, anti-CCR4 antibodies or CCR4 antagonists, comprising determining the level of activity and/or expression of CCR4, CCL17 and/or CCL22 in a tumour sample from the patient. Increased levels of activity and/or expression, whether in absolute terms on a standardized basis having regard to reference values, or whether on a relative (standardized) basis as between (a) tumour/non-tumour cells or (b) tumour cells over time, is generally indicative of a tumour susceptible to treatment with the anti-CCR4 agents disclosed herein.

The invention includes a method of providing information of diagnostic relevance to the diagnosis or treatment of solid tumours, wherein the method comprises determining the amount or activity of CCR4, CCL17 and/or CCL22 in a sample of cells from a patient suspected of having cancer.

The present invention also provides a method of identifying or staging a cancer in an individual comprising determining the level of one or more of the chemokine receptor CCR4, or its ligands CCL22 or CCL17, in a sample of tumour cells obtained from the individual, wherein the cancer is a solid tumour.

Advantageously, the methods of the invention provide a more reliable and more accurate way of identifying, or staging cancer in an individual, or for stratifying individuals for selection of appropriate treatments, particularly in relation to solid tumours, more particularly cervical and oesophageal cancers, but also including cancers selected from the group consisting of bronchial, nasopharyngeal, laryngeal, small cell and non-small cell lung, skin (e.g. melanoma or basal cell carcinoma), brain, pancreatic, neck, lung, kidney, liver, breast, colon, bladder, oesophagus, stomach, cervical, ovarian, germ cell and prostate.

Samples obtained from patients are preferably biopsy samples. A biopsy is a medical test involving the removal of cells or tissues for examination. The tissue is generally examined under a microscope by a pathologist and/or may be analyzed chemically using techniques well known in the art to assess protein or RNA levels. When a smaller sample of tissue is removed, the procedure is called an incisional biopsy or core biopsy. When an entire lump or suspicious area is removed, the procedure is called an excisional biopsy. When a sample of tissue or fluid is removed with a needle, the procedure is called a needle aspiration biopsy.

In alternative embodiments samples may be obtained from patients by other methods well known in the art, including but not limited to, samples of blood, serum, urine, sputum, ascites, intraperitoneal fluids and samples of cells taken by a 'smear' test. Blood samples may be taken via venipuncture, (e.g. by vacuum collection tube or syringe,) catheter, cannula, or by finger prick or heel prick as appropriate to the needs of the patient and the amount of blood required. Once a blood sample has been taken it may be treated prior to analysis (e.g. with sodium citrate, EDTA, ethanol or Heparin) for the purposes of preservation or in order to maximise the accuracy and/or reliability of the signal obtained by analysis of the sample.

Methods of processing (e.g. centrifugation and/or filtration) may be used to separate a blood sample into fractions each of which may be tested independently. For example, a blood serum sample is produced by allowing a whole-blood sample to clot on contact with air where the clotted fraction is removed by centrifugation to leave the serum as the supernatant.

Urine samples are preferably collected by urination or catheterisation.

Sputum samples may be collected from the patient by coughing and/or expectoration, or by extracting a sample with a suction tube or needle inserted in the airway. Preferably sputum samples should have minimal contact with saliva to avoid contamination.

A smear test (for example a Papancolaou test, also called a Pap smear or cervical smear test) may be used to sample cells from a patient. In the case of a cervical smear test cells are collected and removed from the surface of the tissue being tested by means of physical contact with an Aylesbury spatula, plastic fronded 'broom' or other instrument.

The cells and/or liquid collected in a sample taken from a patient may be processed immediately or preserved in a suitable storage medium for later processing. For example, in the case of a cervical smear test the cells are often preserved in an ethanol based storage medium for later processing and analysis. The sample may be treated for the purposes of preservation or for maximising the accuracy and/or reliability of the signal obtained by analysis of the sample. Methods of processing (e.g. centrifugation and/or filtration) may be used to separate a sample into fractions each of which may be tested independently.

In all of the methods and uses of the invention whether hereinbefore or hereinafter defined or described, the cancers are those that give rise to solid humours. The cancer is also preferably one selected from the group consisting of bronchial, nasopharyngeal, laryngeal, small cell and non-small cell lung, skin (e.g. melanoma or basal cell carcinoma), brain, pancreatic, neck, lung, kidney, liver, breast, colon, bladder, oesophagus, stomach, cervical, ovarian, germ cell and prostate. More preferably the cancers are cancers of the cervix, oesophagus, kidney, brain, breast and ovary.

In other embodiments the cancer may be a carcinoma, preferably a squamous cell carcinoma (SCC) or adenocarcinoma, preferably selected from cancers of the cervix, oesophagus, kidney, brain, breast and ovary.

In preferred embodiments, an increased level of CCR4 and/or CCL17 and/or CCL22 produced by the tumour cells identifies a malignant cancer or a prospectively malignant cancer.

The level of one or more of CCR4 and/or CCL17 and/or CCL22 produced in non-tumour cells may be determined and the level in tumour and non-tumour cells compared.

In preferred embodiments the level of CCR4 alone is determined. In other embodiments the level of CCL17 or CCL22 alone is determined.

The level of CCR4 and/or CCL17 and/or CCL22 in tumour cells may be compared with pre-determined levels. Pre-determined levels may be derived from normal non-cancerous tissue, earlier stage cancerous tissue, data obtained from databases or directly from available biological material or samples.

Various ways of determining the level of CCR4 and/or CCL17 and/or CCL22 may be employed in methods of the invention. Preferably the protein level and/or activity of CCR4 and/or CCL17 and/or CCL22 may be used as a measure of the gene products of CCR4 and/or CCL17 and/or CCL22 in the sample.

In a further preferred embodiment, the protein level of CCR4 and/or CCL17 and/or CCL22 is measured using an antibody reactive against CCR4, CCL17 and CCL22 respectively, preferably a specific antibody, e.g. a monoclonal antibody.

The location and amount of specific proteins can be detected by microscopy and histological techniques. Using sample preparation, staining and probing techniques well known in the art, the structure of cells can be shown and specific proteins associated with them can be detected and their location within the sample found.

Histochemical stains are well known in the art and may be used to show cell morphology and/or more specific cellular components. Commonly used stains include hematoxylin (which stains nucleic acids and ergastoplasm, blue) and eosin (which stains elastic and reticular fibres, pink)

Immunohistochemistry is a technique whereby antibodies to specific proteins are used for detection of said proteins in samples. Their binding of antibody to antigen in the sample can be detected in a number of ways.

The most standard method is to conjugate an enzyme that catalyses a colour changing reaction (e.g. alkaline phosphatase, horseradish peroxidase) to the antibody, thus the use of a suitable chromogenic substrate allows visualisation of the location of the antigen under the light microscope. A variation upon this method is immunofluorescence whereby the antibody is conjugated to a fluorophore (e.g. FITC, rhodamine, Texas Red) that emits a detectable signal when excited by a suitable source of energy. Normally this is light of a specific wavelength. Immunofluorescence is advantageous because the use of multiple fluorophores attached to different antibodies allows detection of multiple targets within a sample and is particularly suitable for confocal laser scanning microscopy, which is highly sensitive and can also be used to visualise interactions between multiple proteins. Often detection of the specific antigen is done by a, multiply staged, indirect method. An unlabelled or unconjugated 'primary' antibody, raised against the antigen being tested for is used to bind said antigen. This 'primary' antibody may then be detected by a 'secondary' antibody conjugated to a detectable marker and raised such that it will react with the immunoglobulin of the species that the 'primary' antibody was raised in.

Measurement of protein levels using antibodies may use techniques such as ELISA (Enzyme-linked Immunosorbent Assay), RIA (Radioimmunoassay), EMIT (Enzyme Multiplied Immunoassay Technique), protein microarray analysis, flow cytometry, western blotting, dot blotting or slot blotting, preferably the methodology is quantitative.

Flow cytometry is a technique for counting, examining, and sorting microscopic particles suspended in a stream of fluid. It allows simultaneous multiparametric analysis of the physical and/or chemical characteristics of single cells flowing through an optical and/or electronic detection apparatus.

Fluorescence-activated cell-sorting (FACS) is a specialised type of flow cytometry. It provides a method for sorting a heterogeneous mixture of biological cells into two or more containers, one cell at a time, based upon the specific light scattering and fluorescent characteristics of each cell. It is a useful scientific instrument as it provides fast, objective and quantitative recording of fluorescent signals from individual cells as well as physical separation of cells of particular interest.

The population of cells in a sample is normally heterogeneous. In order to detect the differences between cells, they are treated with chemical and immunochemical techniques similar to those of histochemistry. Immunochemical detection of antigens may be done using antibodies labeled with fluorophores such as FITC, Cy5 and GFP. Staining the cells with dyes (such the DNA binding dyes SYBR-Green and DAPI) may be used to detect differences such as cell size or cell cycle stage within and between samples. Using these techniques in combination allows different cells within the heterogeneous to be given specific fluorescence profiles that are distinguishable by the flow cytometer. In this way cells expressing particular antigens or associated with particular light scattering profiles may be detected and their prevalence, within the sample population, measured.

Alternatively, the level of CCR4 and/or CCL17 and/or CCL22 may be determined by measuring the level of mRNA encoding CCR4 and/or CCL17 and/or CCL22 as a measure of the level of the gene products of CCR4 and/or CCL17 and/or CCL22 in the sample In further preferred embodiments of the invention the mRNA level is measured by a quantitative polymerase chain reaction (qPCR) method, preferably a qPCR method where the template is the product of a reverse transcriptase reaction (RT-qPCR.)

In preferred embodiments mRNA is extracted from the sample and reverse transcribed to produce cDNA prior to qPCR.

In other preferred embodiments the level of transcription of CCR4 and/or CCL17 and/or CCL22 is measured using a nuclease protection assay, preferably the probe used is specific for CCR4 and/or CCL17 and/or CCL22.

In other preferred embodiments of the invention the mRNA level is measured using a DNA microarray.

A DNA microarray (also known as gene or genome chip, DNA chip, or gene array) is a collection of microscopic DNA spots, commonly representing single genes, arrayed on a solid surface by covalent attachment to chemically suitable matrices. Qualitative or quantitative measurements with DNA microarrays utilize the selective nature of DNA-DNA or DNA-RNA hybridization under high-stringency conditions. Fluorophore-based detection may be used to determine the degree of hybridisation from which a quantitative measurement may be calculated.

In preferred embodiments, the cancer is a malignant cancer. Alternatively, the cancer may be a pre-malignant cancer. The method of the invention can advantageously identify the stage to which cancer in a patient has progressed, thereby permitting identification of the most appropriate course of treatment. Consistent with the method of the invention herein before described, including all subsidiary aspects, the invention also provides for the use of CCR4 receptor as a marker for the identification and/or staging of cancer. The CCR4 receptor may be detected by means of an antibody, preferably a specific antibody, e.g. a monoclonal antibody.

Similarly, the invention also provides for the use of CCL17 ligand as a marker for the identification and/or staging of cancer. The CCL17 ligand may be detected by means of an antibody, preferably a specific antibody, e.g. a monoclonal antibody.

The invention also provides for the use of CCL22 ligand as a marker for the identification and/or staging of cancer. The CCL22 ligand may be detected by means of an antibody, preferably a specific antibody, e.g. a monoclonal antibody.

The invention includes a method of treating or preventing malignant disease in an individual suffering from cancer comprising treating the individual with an effective amount of antibodies reactive against reactive against CCR4 and/or CCL17 and/or CCL22. The invention therefore provides the use of antibodies reactive against CCR4 and/or CCL17 and/or CCL22 for the manufacture of a medicament for the treatment or prevention of cancer in an individual suffering from cancer.

In a further embodiment of the invention antibodies reactive against CCR4 and/or CCL17 and/or CCL22 may be used in the manufacture of a medicament for the treatment or prevention of cancer.

In a preferred embodiment, the medicament comprises an antibody specific for CCR4, and may be a monoclonal antibody.

Embodiments of this aspect of the invention are, for example, the antibodies disclosed in WO0164754 (Kyowa Hakko Kogyo), WO05035582 (Kyowa Hakko Kogyo), WO03018635 (Kyowa Hakko Kogyo), WO05053741 (Kyowa Hakko Kogyo) or WO0042074 (MILLENIUM PHARMACEUTICALS);

In an additional preferred embodiment, the medicament comprises an antibody specific for CCL17, and may be a monoclonal antibody.

In an additional preferred embodiment, the medicament comprises an antibody specific for CCL22, and may be a monoclonal antibody.

In another embodiment, the medicament comprises an antibody which may be a Fab fragment wherein said Fab fragment may be selected from the group consisting of: scFv, F(ab')$_2$, Fab, Fv and Fd fragments; or CDR3 regions.

The fragment antigen binding (Fab fragment) is a region on an antibody which binds to antigens. It is composed of one constant and one variable domain of each of the heavy and the light chain. These domains shape the paratope—the antigen binding site—at the amino terminal end of the monomer. The two variable domains bind the epitope on their specific antigens.

Fc and Fab fragments can be generated. The enzyme papain can be used to cleave an immunoglobulin monomer into two Fab fragments and an Fc fragment. The enzyme pepsin cleaves below the hinge region, so a F(ab')2 fragment and a Fc fragment may be formed. The variable regions of the heavy and light chains can be fused together to form a single chain variable fragment (scFv), which is only half the size of the Fab fragment yet retains the original specificity of the parent immunoglobulin.

A complementarity determining region (CDR) is a short amino acid sequence found in the variable domains of antigen receptor (e.g. immunoglobulin and T cell receptor) proteins that complements an antigen and therefore provides the receptor with its specificity for that particular antigen. Most of the sequence variation associated with immunoglobulins and T cell receptors are found in the CDR regions, these regions are sometimes referred to as hypervariable domains. Among these, CDR3 shows the greatest variability as it is encoded by a recombination of the VJ regions.

In another embodiment, the medicament comprises antibodies that may be humanised or chimeric antibodies.

Humanized antibodies or chimeric antibodies are a type of monoclonal antibody that are synthesized using recombinant DNA technology to circumvent the clinical problem of immune response to foreign antigens. The standard procedure of producing monoclonal antibodies yields mouse antibodies. Although murine antibodies are very similar to human antibodies the differences are significant enough that the human immune system recognizes mouse antibodies as foreign, rapidly removing them from circulation and causing systemic inflammatory effects. Humanized antibodies may be produced by merging the DNA that encodes the binding portion of a monoclonal mouse antibody with human antibody-producing DNA. Mammalian cell cultures are then used to express this DNA and produce these part-mouse and part-human antibodies that are not as immunogenic as the purely murine variety.

Modifications may be made to monoclonal antibodies that bind only to cell-specific antigens and preferably induce an immunological response against the target cancer cell. Such monoclonal antibodies are preferably modified for delivery of a toxin, radioisotope, cytokine or other active conjugate.

In another aspect of antibody technology, bispecific antibodies may be designed that can bind with their Fab regions both to target antigen and to a conjugate or effector cell. Also, all intact antibodies can bind to cell receptors or other proteins with their Fc region.

The production of recombinant monoclonal antibodies may also involve technologies, referred to as repertoire cloning or phage display/yeast display. These may involve the use of viruses or yeast to create antibodies, rather than mice. These techniques rely on rapid cloning of immunoglobulin gene segments to create libraries of antibodies with slightly different amino acid sequences from which antibodies with desired specificities can be selected. This process can be used to enhance the specificity with which antibodies recognize antigens, alter their stability in various environmental conditions, increase their therapeutic efficacy, and modulate their detectability in diagnostic applications.

The invention includes a method of treating or preventing malignant disease in an individual suffering from cancer comprising treating the individual with an effective amount of a small molecule inhibitor of CCR4 and/or CCL17 and/or CCL22. The invention therefore provides the use of small molecule inhibitor of CCR4 and/or CCL17 and/or CCL22 for the manufacture of a medicament for the treatment or prevention of cancer in an individual suffering from cancer.

Embodiments of this aspect of the invention are, for example, the small molecule inhibitors disclosed in WO04007472 (ONO PHARMACEUTICAL CO.), WO05023771 (ONO PHARMACEUTICAL CO.), WO02094264 (TULARIK INC.), WO0230358 (TULARIK/CHEMOCENTRYX), WO0230357 (CHEMOCENTRYX), WO051236976 (ASTELLAS PHARMA INC.), WO05085212 (YAMANOUCHI PHARMACEUTICAL CO., LTD.), WO05082865 (YAMANOUCHI PHARMACEUTICAL CO., LTD.), WO04108717 (ASTRAZENECA AB), EP1633729 (ASTRAZENECA AB) or WO03014153 (TOPIGEN PHARMACEUTIQUE INC.)

The invention also includes a method of treating or preventing malignant disease in an individual suffering from cancer comprising treating the individual with an effective amount of an agent that modulates the activity of CCR4 and/or CCL17 and/or CCL22. The invention therefore provides the use of an agent that modulates the activity of CCR4 and/or CCL17 and/or CCL22 for the manufacture of a medicament for the treatment or prevention of cancer in an individual suffering from cancer.

Embodiments of this aspect of the invention are, for example, the CCR4 modulating agents as disclosed in WO0041724A1 (LELAND STANFORD/LEUKOSITE);

In preferred aspects, the method and use of the invention are for the treatment of cancer, preferably selected from the group consisting of bronchial, nasopharyngeal, laryngeal, small cell and non-small cell lung, skin (e.g. melanoma or basal cell carcinoma), brain, pancreatic, neck, lung, kidney, liver, breast, colon, bladder, oesophagus, stomach, cervical, ovarian, germ cell and prostate. More preferably the cancers are cancers of the cervix, oesophagus, kidney, brain, breast and ovary.

In particularly preferred treatments the cancer is cervical cancer, preferably squamous cell carcinoma (SCC).

In particularly preferred treatments the cancer is oesophageal cancer, preferably squamous oesophageal carcinoma.

In another aspect, the invention provides a method of screening for anti-cancer agents comprising the steps of:
 a) providing test cells that express the CCR4 receptor and that are capable of, or are in the process of, proliferation,
 b) exposing the test cells to a candidate agent for a period of time,
 c) measuring proliferation of the test cells, whereby a decrease in any proliferation in the test cells identifies an anti-cancer agent and/or increased or continued proliferation of the test cells identifies a poor or inactive anti-cancer agent.

In other aspects, the invention provides a method of screening for anti-cancer agents comprising the steps of:
 a) providing test cells expressing the CCR4 receptor and that are capable of, or are in the process of, proliferation,
 b) providing at least first and second aliquots of said cells,
 c) exposing said first aliquot to a candidate agent for a period of time,
 d) not exposing said second aliquot to the candidate agent for the period of time,
 e) measuring the degree of proliferation of the cells in the first and second aliquots, whereby a decrease in any proliferation of the cell(s) in the first aliquot relative to the cell(s) in the second aliquot identifies an anti-cancer agent and/or increased or continued proliferation of the cell(s) in the first aliquot relative to the cell(s) in the second aliquot identifies a poor or inactive anti-cancer agent.

In certain preferred embodiments, the test cells are induced to proliferate, preferably prior to exposure to the candidate agent.

In other preferred embodiments, the test cells are induced to proliferate by the addition of a ligand of the CCR4 receptor.

In another aspect, the invention provides a method of screening for anti-cancer agents comprising the steps of:
 a) providing test cells that express the CCR4,
 b) exposing the test cells to a candidate agent for a period of time,
 c) measuring the level of a secreted protein or signalling molecule of the test cells, whereby a decreased level of the secreted protein or signalling molecule identifies an anti-cancer agent and/or no decrease or an increased level of secreted molecule or signalling molecule identifies a poor or inactive anti-cancer agent.

In other aspects, the invention provides a method of screening for anti-cancer agents comprising the steps of
 a) providing test cells expressing the CCR4,
 b) providing at least first and second aliquots of said cells,
 c) exposing said first aliquot to a candidate agent for a period of time,
 d) not exposing said second aliquot to the candidate agent for the period of time,
 e) measuring the level of a secreted protein or signalling molecule of the test cells in the first and second aliquots, whereby a decreased level of the secreted protein or signalling molecule by the cell(s) in the first aliquot relative to the cell(s) in the second aliquot identifies an anti-cancer agent and/or no decrease or an increased level of secreted molecule or signalling molecule from the cell(s) in the first aliquot relative to the cell(s) in the second aliquot identifies a poor or inactive anti-cancer agent.

In preferred embodiments, the secreted protein or signalling molecule is a cytokine or chemokine.

In other preferred embodiments, the level of the secreted protein or signalling molecule is measured at any time before, during or after exposure of the test cells to the candidate agent.

In certain preferred embodiments, test cells are induced to secrete a particular protein, or other signalling molecule, preferably a chemokine or cytokine, preferably prior to exposure to the candidate agent.

In other preferred embodiments, test cells are induced to secrete a particular protein, or other signalling molecule, preferably a chemokine or cytokine, by the addition of a ligand of the CCR4 receptor.

In another aspect, the invention provides a method of screening for anti-cancer agents comprising the steps of
 a) providing test cells that are expressing the CCR4 receptor and that are capable of, or are in the process of, migration.
 b) exposing the test cells to a candidate agent for a period of time.
 c) simultaneously or subsequent to the period of exposure, providing conditions suitable for cell migration, and measuring any migration of exposed cells, whereby reduced or absent migration in the exposed cells identifies an anti-cancer agent and/or increased or continued migration of the test cells identifies a poor or inactive anti-cancer agent.

A method of screening for anti-cancer agents comprising the steps of:
 a) providing test cells expressing the CCR4 receptor and that are capable of, or are in the process of migration,
 b) providing at least first and second aliquots of said cells,
 c) exposing said first aliquot to a candidate agent for a period of time,
 d) not exposing said second aliquot to the candidate agent for the period of time,
 e) simultaneously or subsequent to the period of exposure, providing conditions suitable for cell migration, and measuring the degree of migration of the cell(s) in the first aliquot relative to the cell(s) in the second aliquot, whereby reduced or absent migration identifies an anti-cancer agent and/or increased or continued proliferation of the cell(s) in the first aliquot relative to the cell(s) in the second aliquot identifies a poor or inactive anti-cancer agent.

Chemotaxis, is the phenomenon in which bodily cells, bacteria, and other single-cell or multicellular organisms direct their movements according to certain chemicals in their environment. This is important for bacteria to find food (e.g. glucose) by swimming towards the highest concentration of food molecules, or to flee from poisons (e.g. phenol). In multicellular organisms, chemotaxis and cell migration are critical to development as well as normal function. In addition, it is known in the art that mechanisms that allow chemotaxis and cell migration in animals can be subverted during cancer metastasis.

Chemotaxis is called positive if movement is in the direction of a higher concentration of the chemical in question, and negative if the direction is opposite.

In haptotaxis the gradient of the chemoattractant is expressed or bound on a surface, in contrast to the classical way of chemotaxis when the gradient develops in a soluble space.

Necrotaxis embodies a type of chemotaxis when the chemoattractant molecules are released from necrotic or apoptotic cells. Depending on the chemical character of released substances necrotaxis can accumulate or repel cells, which underlines the pathophysiological significance of this phenomenon.

In certain preferred embodiments, the test cells are induced to migrate, preferably prior to exposure to the candidate agent.

In other preferred embodiments, the test cells are been induced to migrate by the addition of a ligand of the CCR4 receptor.

Cell migration and cell invasion assays measure the ability of certain cell types to move through a porous membrane or matrix toward a chemoattractant or growth factor. Cell migration and invasion may be critical processes in angiogenesis and tumour metastasis. Cell invasion may be measured in one or more dimensions by using suitable culture conditions and a suitable porous matrix for the cells to move through.

In accordance with preferred screening methods, cell invasion may be measured preferably using a matrigel Boyden chamber.

In the method aspects of the invention defined herein the ligand may be CCL17 and/or the ligand may be CCL22.

In another aspect, the invention provides a method of screening for anti-cancer agents comprising the steps of:
 a) providing cancer cells that express the CCR4 receptor,
 b) culturing the cancer cells under conditions that result in at least some cancer cell death,
 c) exposing the test cells to a candidate agent for a period of time,
 d) measuring death of cancer test cells, whereby no or no significant increase in cell death in the test cells identifies a poor or inactive anti-cancer agent and/or increased cell death identifies an anti-cancer agent.

In other aspects, the invention provides a method of screening for anti-cancer agents comprising the steps of:
 a) providing cancer cells that express the CCR4 receptor,
 b) providing at least first and second aliquots of said cells,
 c) culturing the cancer cells under conditions that result in at least some cancer cell death,
 d) exposing said first aliquot to a candidate agent for a period of time,
 e) not exposing said second aliquot to the candidate agent for the period of time,
 f) measuring death of cancer test cells in the first and second aliquots, whereby no or no significant increase in cell death in the first aliquot relative to the cell(s) in the second aliquot identifies a poor or inactive anti-cancer agent and/or increased cell death in the first aliquot relative to the cell(s) in the second aliquot identifies an anti-cancer agent.

In other preferred embodiments the exposure of the test cells or cancer cells to candidate agent may be before or after the change in culture conditions.

In preferred embodiments or methods of screening for anti-cancer agents, the test cells or cancer cells are capable of, or are in the process of, proliferation.

In methods of screening for anti-cancer agents, the cell or cells may be from a tumour biopsy sample or may be cervical cancer cell(s), e.g. C-41 (ATCC, Rockville Md., USA) or another cell line endogenously expressing CCR4.

The invention will now be described in detail, including by way of experimental examples and with reference to the drawings in which:

(A) Summary of the percentage of samples expressing CC and CXC chemokine receptor mRNA in non-neoplastic (white bars) and malignant (black bars) cervical tissue after ribonuclease protection assay (RPA) for mRNA expression.

(B) RPA of non-neoplastic tissue samples 1 to 14 and malignant tissues: Adenocarcinoma biopsies, samples 1 to 4 and squamous cell carcinoma (SCC) biopsies, samples 1 to 11. Stages of adenocarcinoma tissues were: 1 to 3, 1B1; 4, 1B2. Stages of SCC were: 1, 1A2; 2 to 8-11, 1B1; 9, 1B2 and 10, 2A.

(C) Up-regulation of CCR4 gene expression in epithelial and stromal compartments when compared to their non-neoplastic counterparts. mRNA expression in non-neoplastic cervical tissue was used as a baseline to compare malignant tissue mRNA and is represented as value "1".

Figure 2:
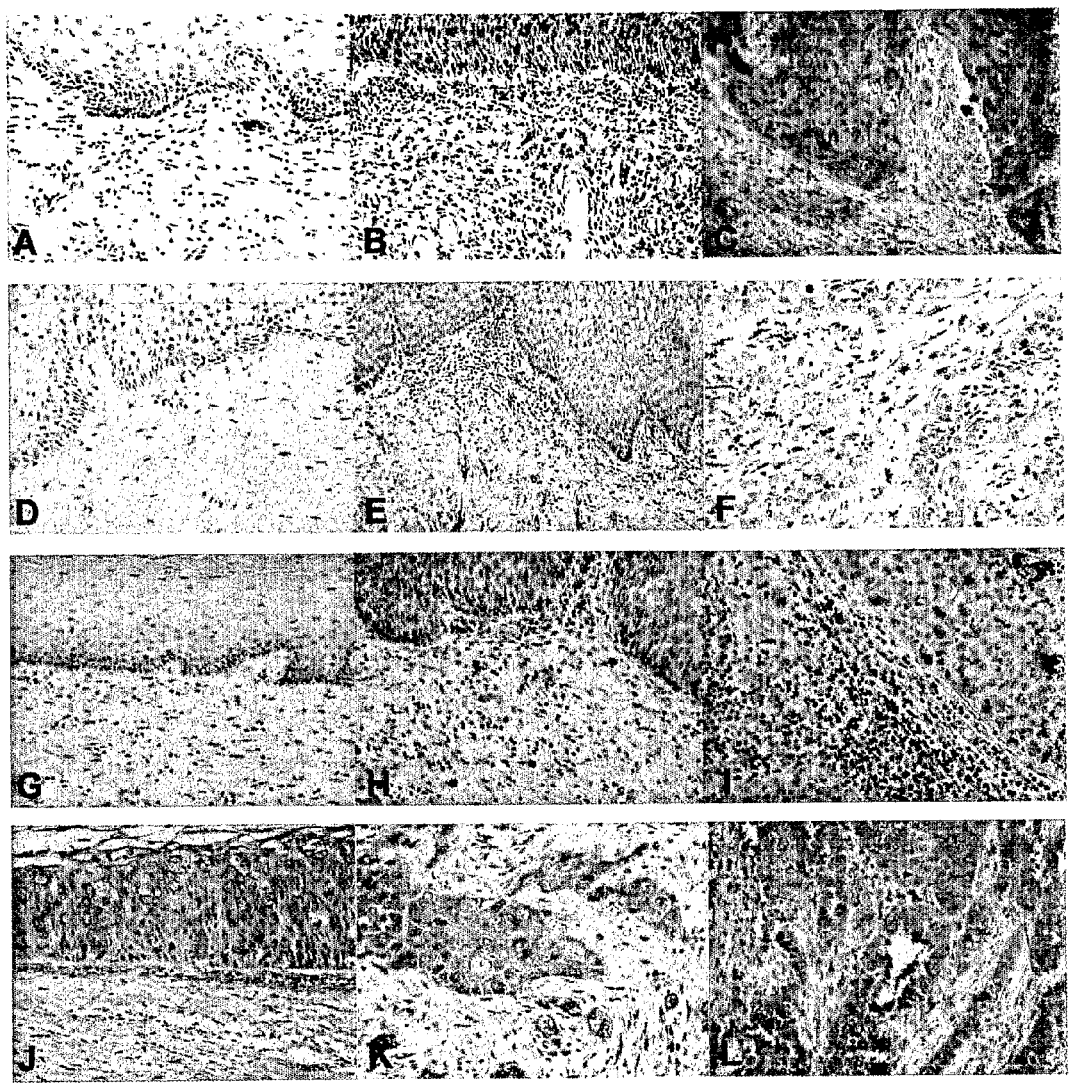

FIG. 2-Immunohistochemistry for CCR4 during malignant progression of the cervix

CCR4 protein expression in the stroma of (A) non-neoplastic cervical tissue, 200×; (B) CIN 200×; (C) invasive cervical tissue, 200×. CD68+ protein expression in (D) normal, 400×: (E) CIN, 200×: and (F) invasive cervical cancer, 400×. FoxP3+ protein staining in (G) non-neoplastic cervical tissue, 200×; (H) CIN, 400×; and (I) invasive cervical cancer, 400×. Epithelial CCR4 protein expression in (J) non-neoplastic, 200×; (K) CIN, 400× and (L) invasive cervical cancer, 400×.

Figure 3:
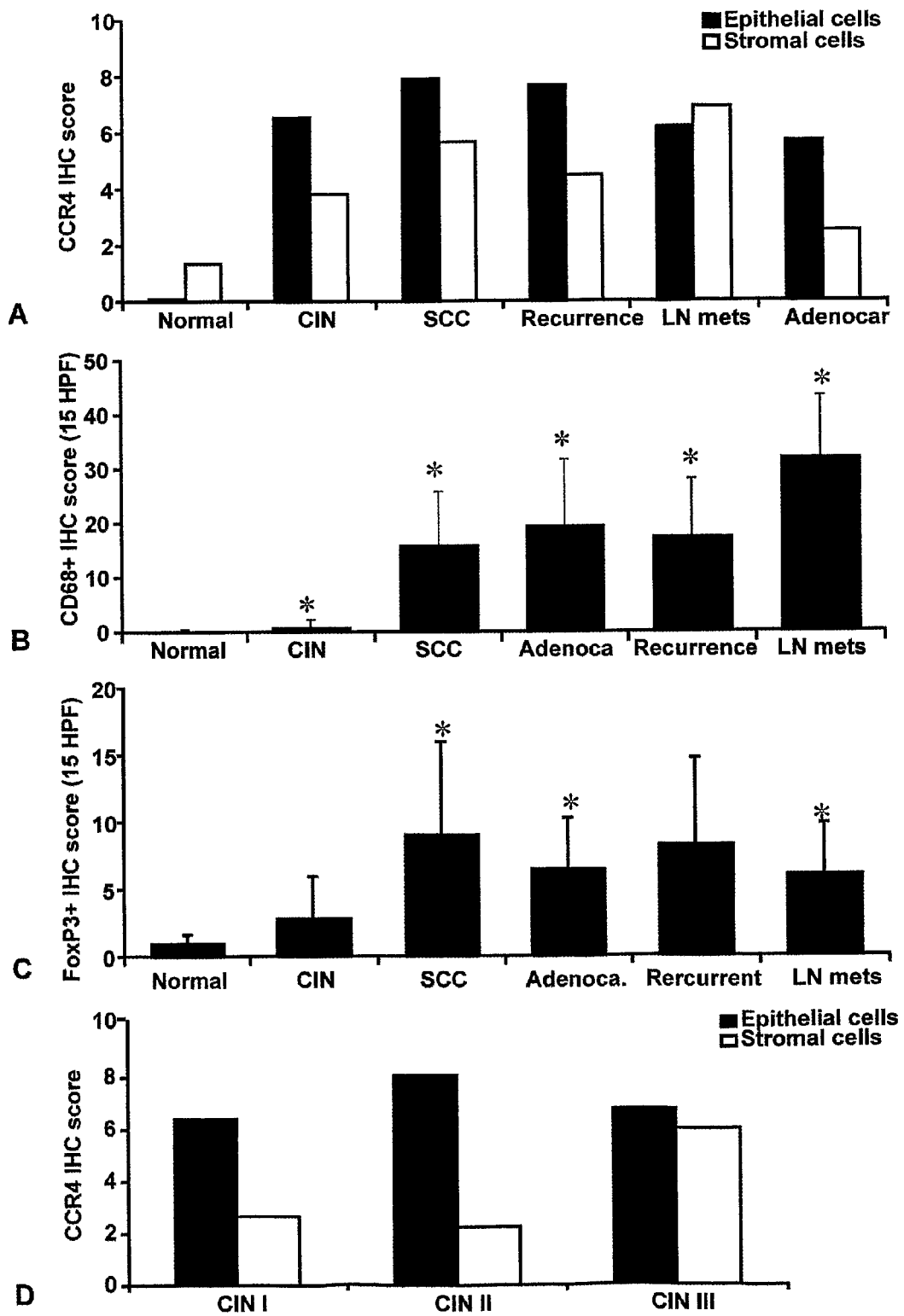

FIG. 3—Immunohistochemistry score for CCR4, CD68 and FoxP3 positive cells during malignant progression of the cervix (A) Total score for epithelial cell (black bars) and stromal cell (white bars) staining for CCR4, calculated by 'positivity'×'intensity" in normal (n=23), CIN (n=63) and SCC (n=45), recurrent cancer (n=15), lymph node metastasis (n=10) and adenocarcinoma (n=10). (B) Mean CD68+ score (+SE) of intra- and peritumoral macrophage infiltration in normal (n=11), CIN (n=16), adenocarcinomas (n=16), recurrent cancer (n=24) and metastatic deposits in lymph nodes (n=11); ** p<0.001; p<0.005. (C) Mean FoxP3+ score (+SE) of intra and peritumoral Treg cell infiltration in normal (n=11), CIN (n=16), SCC (n=44), adenocarcinomas (n=16) recurrent cancers (n=24) and metastatic deposits in the lymph node (n=11), * p<0.01. (D) Total CCR4 score on epithelial cells (black bars) and stromal cells (white bars) calculated by 'positivity'×'intensity' in CIN I (n=26), CIN II (n=19) and CIN III (n=17).

Figure 4:
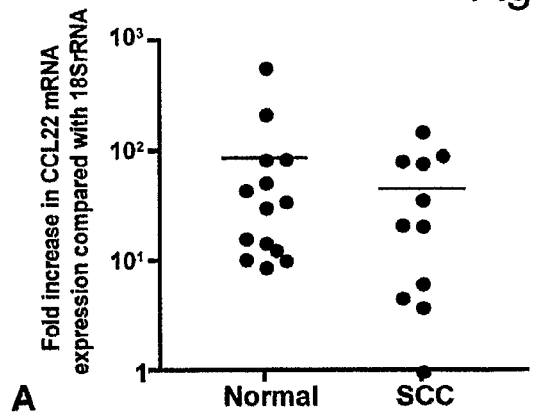
Figure 4:
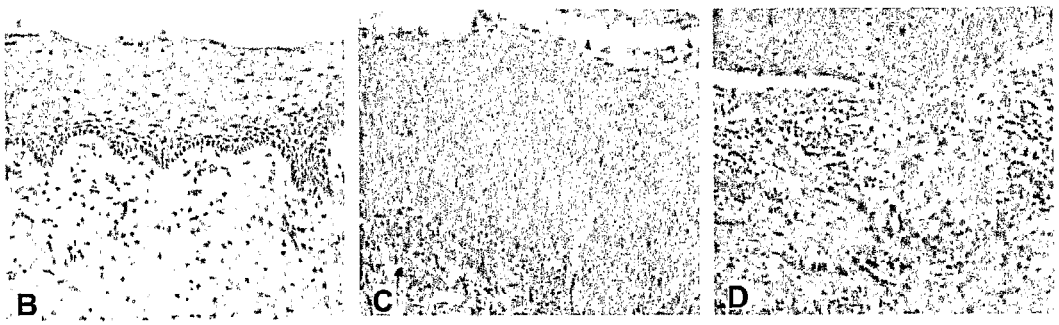
Figure 4:
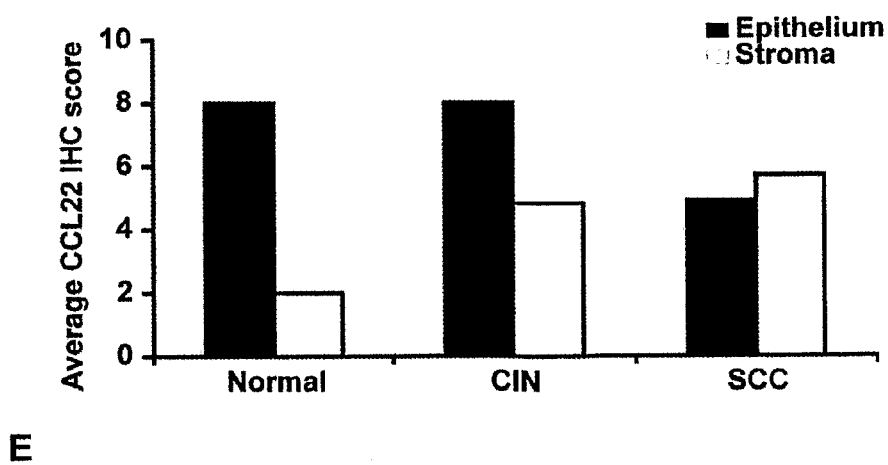

FIG. 4—mRNA and protein expression of the CCR4 ligand CCL22 in normal, CIN and SCC cervix (A) CCL22 mRNA expression levels as assessed by quantitative Real Time RT-PCR in normal (n=14) and SCC (n=11) cervical biopsies (P=0.43). CCL22 protein expression in (B) non-neoplastic, 200×; (C) CIN, 200× and (D) SCC, 200× cervical tissues. (E) Total CCL22 score of epithelial cells (black bars) and stromal cells (white bars) calculated by 'Positivity×Intensity' in normal (n=16), CIN (n=17), SCC (n=19) and adenocarcinomas (n=5) samples of the cervix.

Figure 5:
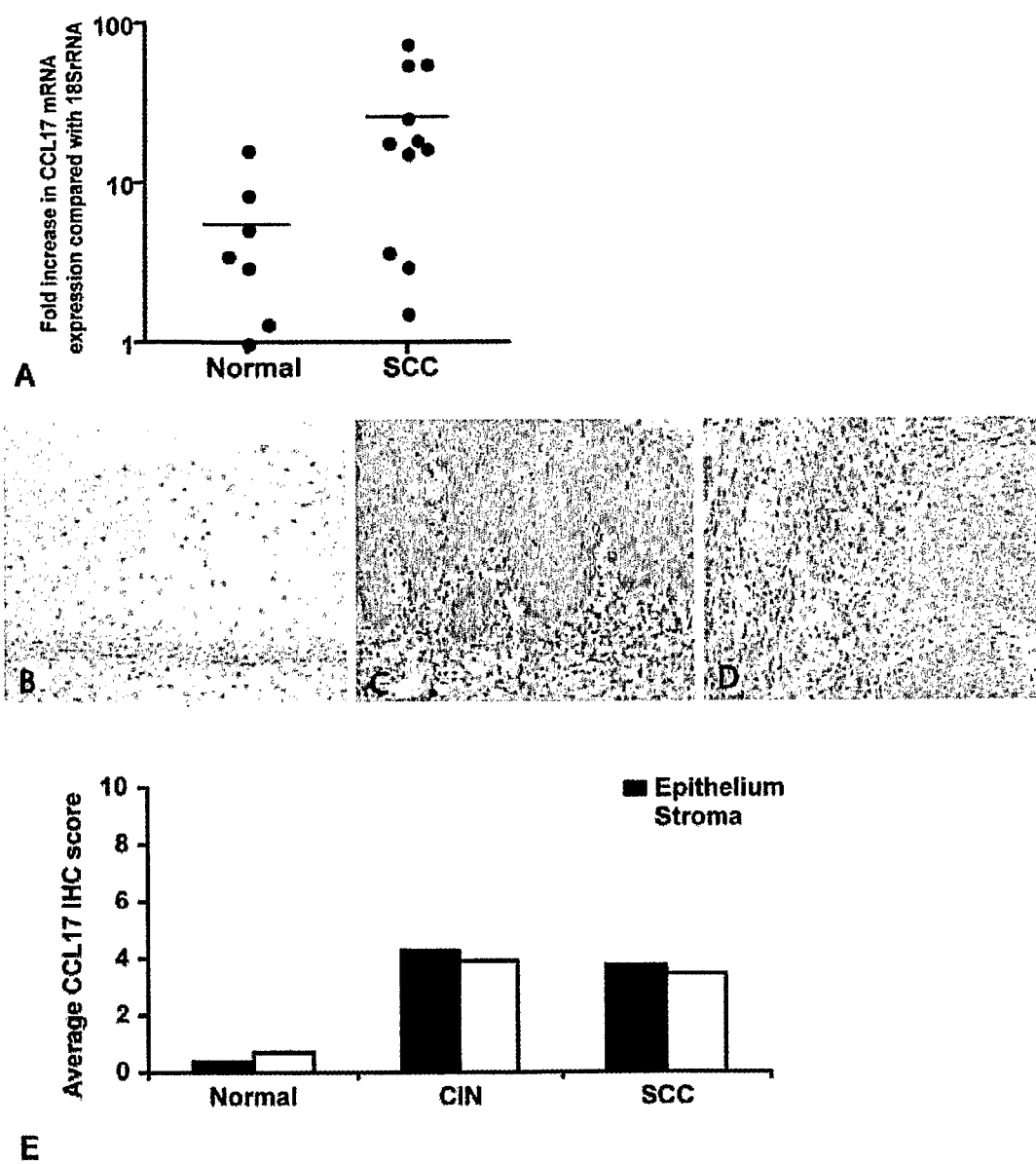

FIG. 5—mRNA and protein expression of the CCR4 ligand CCL17 in normal, CIN and SCC cervix (A) CCL17 mRNA expression levels as assessed by quantitative Real Time RT-PCR in normal (n=7) compared with SCC (n=11) cervical biopsies (P=0.02). CCL17 protein expression in (B) non-neoplastic, 200×; (C) CIN, 200× and (D) SCC, 200×. (E) Total CCL17 score of epithelial cells (black bars) and stromal cells (white bars) calculated by 'positivity×intensity' in normal (n=21), CIN (n=33), SCC (n=20) and adenocarcinomas (n=4) samples of the cervix.

Figure 6:
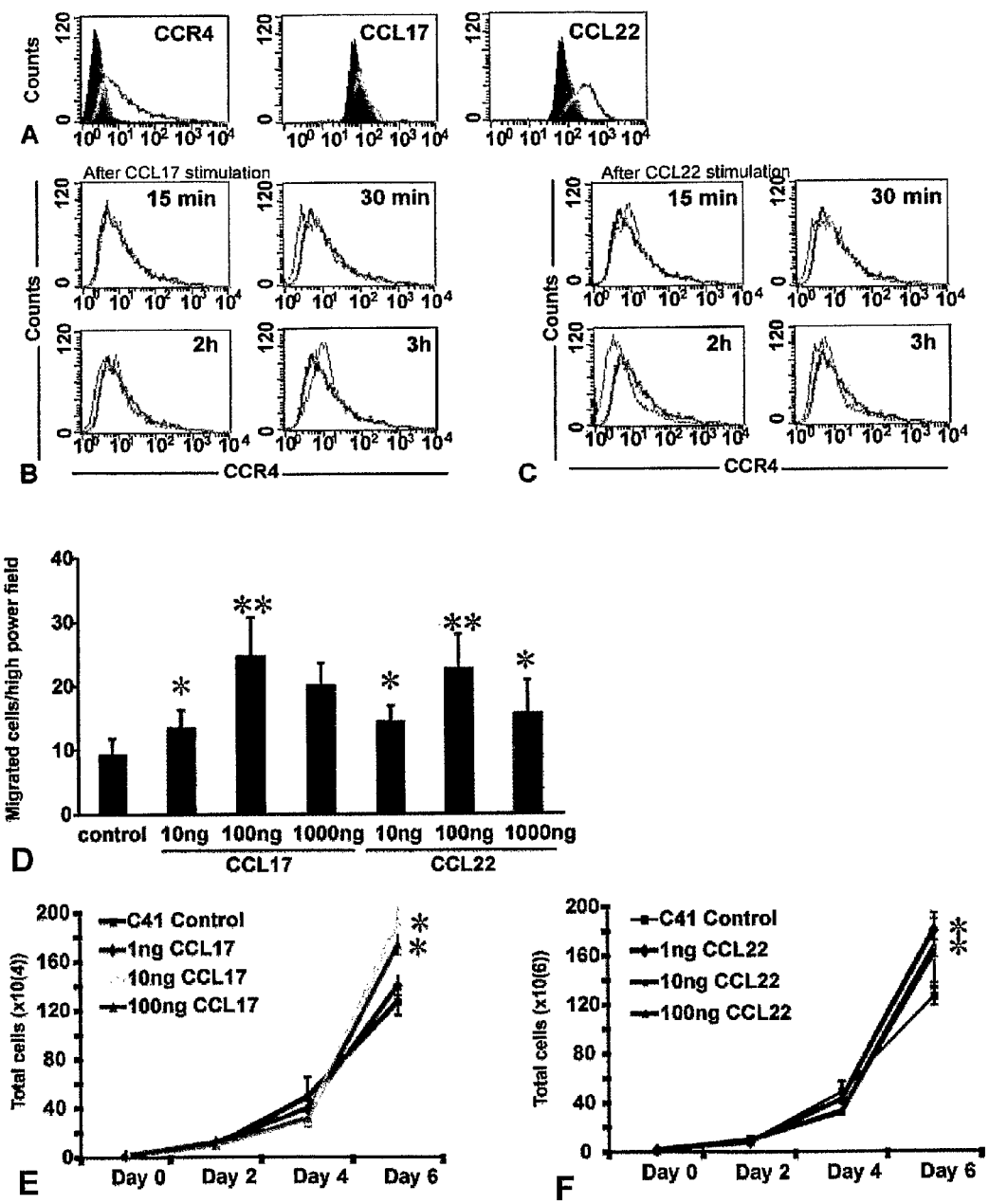

FIG. 6—CCR4 is functional on the cervical cancer cell line C-41

(A) CCR4, CCL17 and CCL22 protein expression (blue lines) was measured in the C-41 cervical cancer cell line by using flow cytometry. Expression/internalization of CCR4 by C-41 was examined after 100 ng/ml (B) of CCL17 and (C) CCL22 stimulation (blue line represents CCR4 control at 0 minutes; orange line indicates CCR4 protein expression after stimulation with the appropriate ligand). (D) Migration of the C-41 cervical cancer cell in response to CCL17 and CCL22. Values are the mean±SD of 10 determinations, * $P<0.05$, ** $P<0.01$. (E and F) C-41 growth under suboptimal conditions after stimulation of 1 ng/ml, 10 ng/ml and 100 ng/ml of CCL17 and CCL22 for 2, 4 and 6 days. After 6 days C-41 showed in significant growth increase after stimulation with 10 ng/ml CCL17; (P=0.017) and 100 ng/ml CCL17 (P=0.044), but not with 1 ng/ml CCL17 (P=0.383). Stimulation of 1 ng/ml CCL22 and 100 ng/ml CCL22 also showed significant increased growth: 1 ng/ml CCL22; (P=0.026) and 100 ng/ml CCL22 (P=0.043), but not with 10 ng/ml CCL22 (P=0.195).

Figure 7:
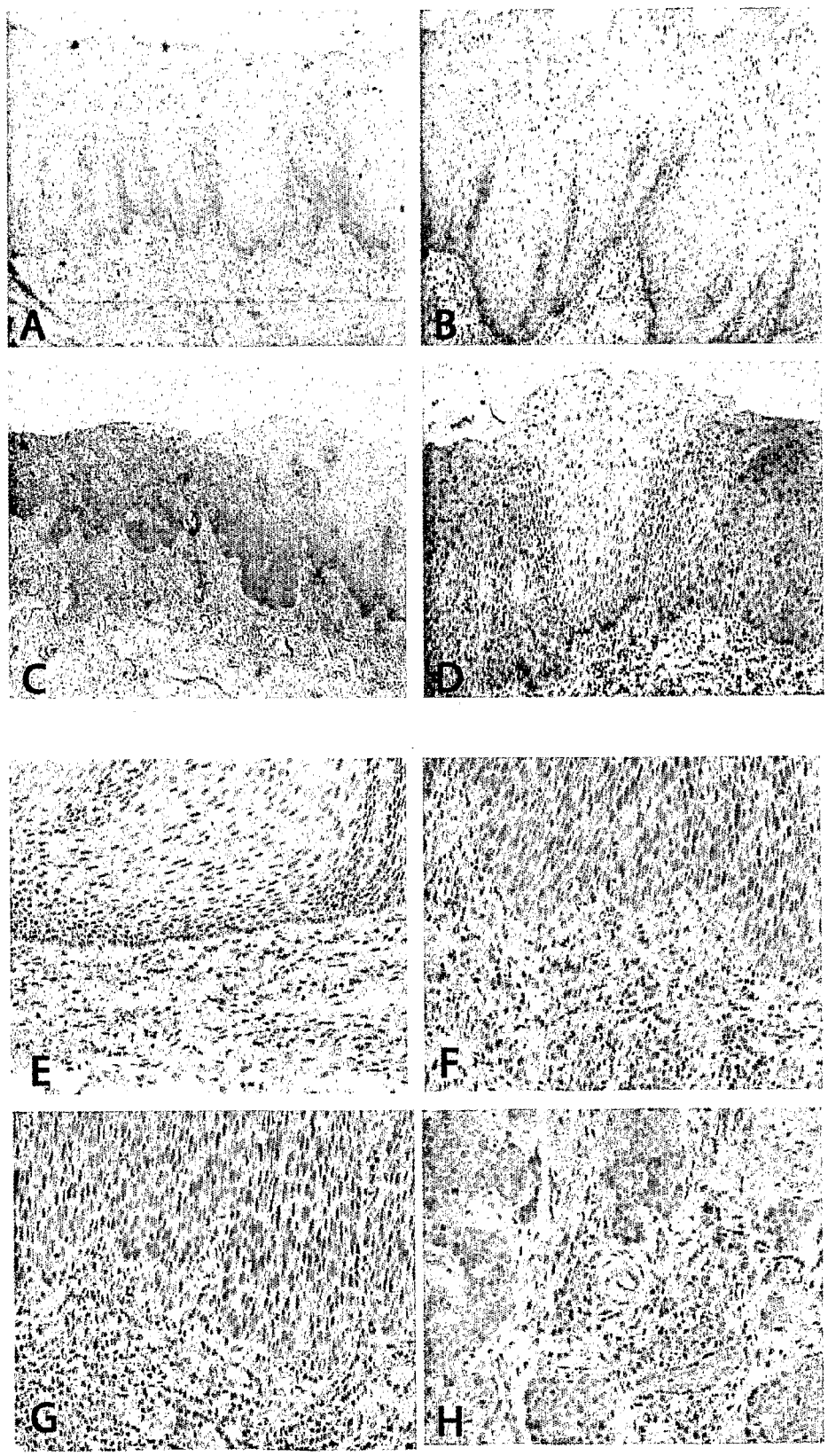

FIG. 7—CCR4 expression in carcinogenesis of oesophagus CCR4 expression in normal (A, ×40; D, ×40), hyperplastic (B, ×100), dysplastic (C, ×40; D, ×40) epithelial cells of oesophagus and invasive cancer cells (H, ×200). CCR4 expression in the stroma during carcinogenesis of oesophagus: E, normal oesophagus (×200); F, dysplasia I (×200); G, dysplasia III (×200); H, invasive cancer (×200).

FIG. 8—Immunohistochemistry scoring results of CCR4 positive stromal cells during malignant progression of the cervix Scoring was assessed by number of cells positive for CCR4 and by intensity of CCR4 staining. Number of cells was measured as average of 15 HPF: 0=no CCR4 protein expression; +1=1-10 CCR4 positive cells per HPF; +2=10-20 positive cells per HPF; +3 (21-30 cells per HPF); +4 (>30 cells). Intensity was measured as: 0=no expression; 1+=mild expression; 2++=moderate expression; 3+++=strong expression.

Figure 10A:
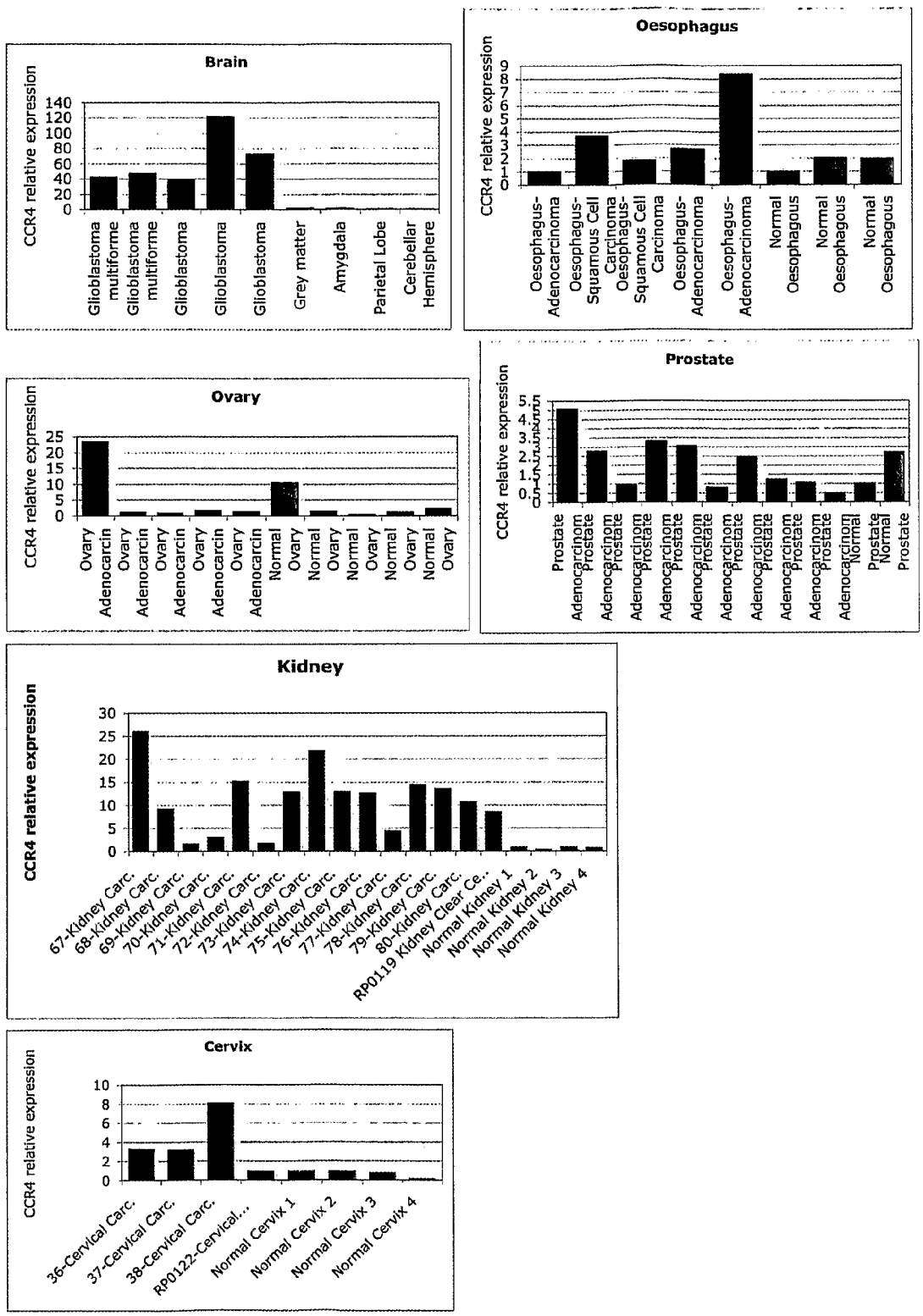
Figure 10B:
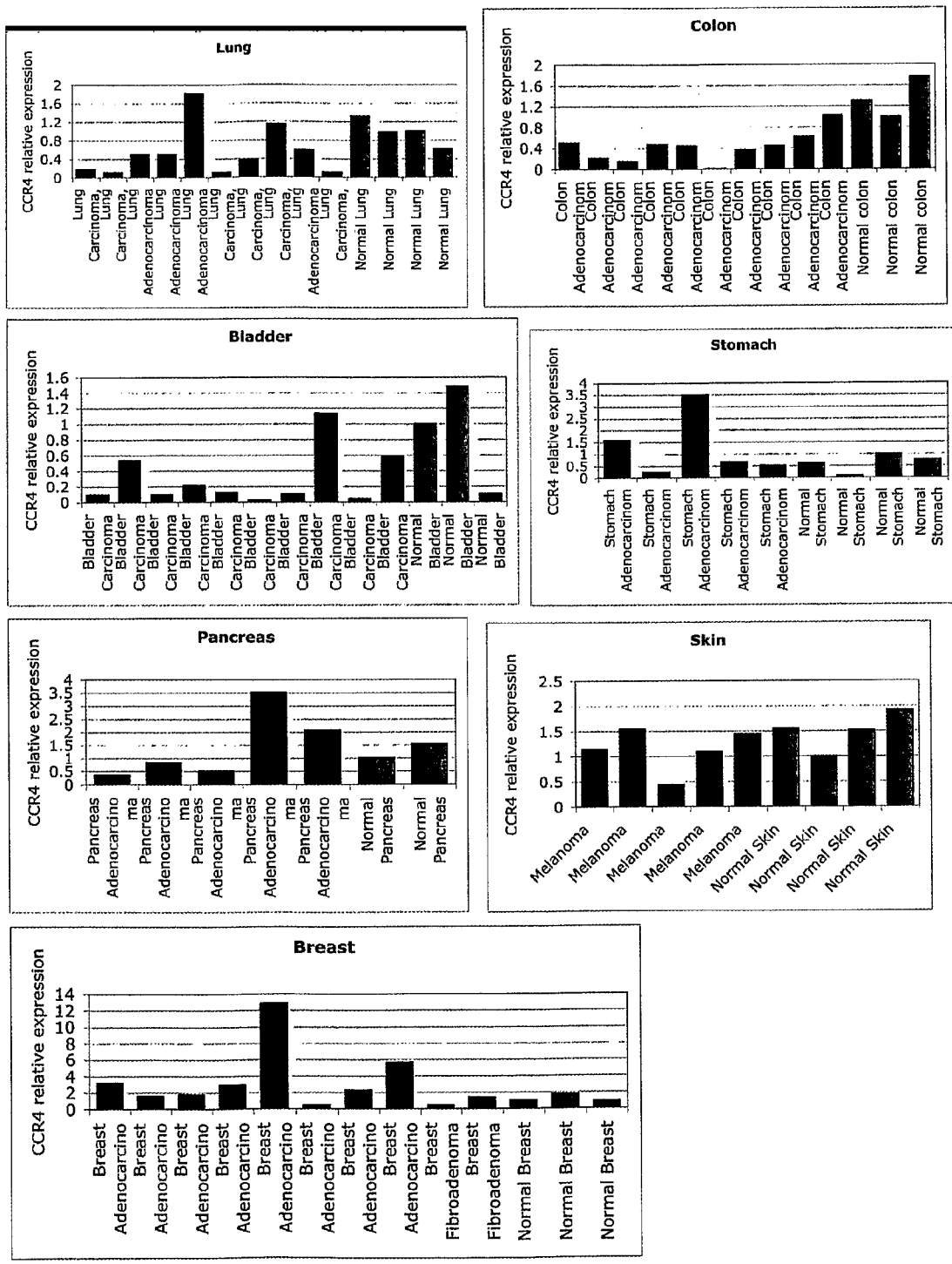

FIG. 9—Immunohistochemistry scoring results of CCR4 positive epithelial cells during malignant progression of the cervix Scoring was assessed by number of cells positive for CCR4 and by intensity of CCR4 staining. 0=no CCR4 protein expression on epithelial cells; +1=less than 25% of the section has CCR4 expression; +2=26-50% cells positive; +3=51-75% cells positive; +4 more than 76% cells CCR4 positive. Intensity was measured as: 0=no expression; 1+=mild expression; 2++=moderate expression; 3+++=strong expression FIG. 10—The results of a screen for CCR4 expression in a wider range of tumours using a human tissue-derived cDNA library (Cancer Research UK). The library contains cDNA generated from RNA isolated from 5-10 tumour samples and 2-5 normal samples for 11 different tumour types: lung, colon, bladder, stomach, pancreas, skin, breast, brain, oesophagus, ovary and prostate. The CCR4 mRNA expression levels were measured using quantitative Real Time RT-PCR.

Figure 11:
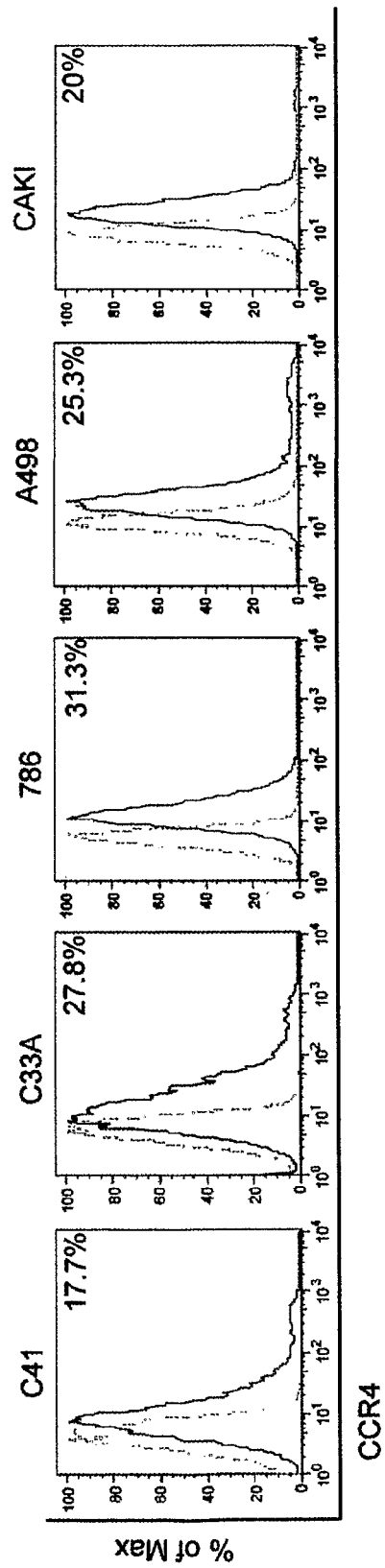
Figure 12:
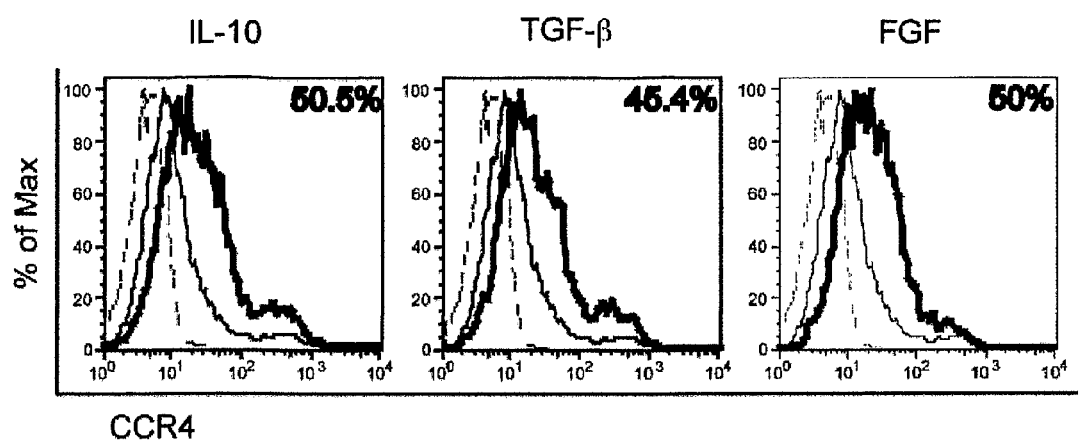

FIG. 11 shows the results of FACS analysis for CCR4 expression on cervical cell lines (C41, C33A) and renal cancer cell lines (786, A498, CAKI). Dashed line: isotype-matched control antibody; grey line CCR4 expression FIG. 12 shows the results of FACS analysis of CCR4 expression on C41 cells after 24 h stimulation with IL-10, TGF-β and FGF. Dashed line: isotype control; grey line CCR4 expression; bold line; CCR4 expression after cytokine stimulation.

FIG. 13 shows a cDNA sequence of CCR4. This is SEQ ID NO:1 referred to herein.

DETAILED DESCRIPTION OF THE INVENTION

The inventors have discovered that chemokine receptor CCR4 expression is an early event in carcinogenesis in certain tumour types. Epithelial expression of a receptor for homeostatic chemokines usually present in a tissue may confer a survival advantage on the initiated cell.

The chemokine receptor CCR4 was present on dysplastic non-invasive lesions of the cervix and oesophagus. This was particularly striking in some of the oesophageal cancer samples where CCR4 positive dysplastic areas were clearly seen adjacent to normal epithelial areas in the same section (e.g. FIGS. 7 C and D).

The chemokine receptor CCR4 increased with malignant progression of the cervix. This was not only due to increased infiltration of CCR4-positive macrophages and Treg cells, but also to acquisition of CCR4 expression by epithelial cells. An unexpected finding was that CCR4 was strongly expressed on non-invasive epithelial cells in intraepithelial (CIN) lesions as well as invasive cancer cells. Progression from CIN to invasive disease was associated with increased stromal cell expression of CCR4 ligands CCL17 and 22 and these chemokines stimulated growth and migration of a CCR4-positive cervical cancer cell line (e.g. FIG. 4 and FIG. 6). CCR4 was also detected on dysplastic as well as invasive epithelial cells in oesophageal cancer, again with CCL17 and CCL22 levels increasing during malignant progression. Changes in CCL17 and 22 gradients aid transition from pre-invasive to invasive disease and attract tumour-promoting leucocytes that help initiated cells evade immune surveillance.

The two CCR4-binding chemokines, CCL17 and CCL22, were also found on the surface of blood and lymphatic vessels in the tumour biopsies. It was not possible to quantify this but preliminary observations indicate an increase in the intensity of staining with malignant progression.

Another element of the CCR4 system is the non-signalling chemokine receptor D6 that has a high affinity for CCL17 and CCL22 [18]; its presence in the tissues would be expected to influence gradients of these chemokines [19].

FIG. 6 shows that the CCR4 receptor is functional on the cervical cancer cell line C-41. CCR4 can be up-regulated by the microenvironment. CCR4 positive and negative cells were exposed to a number of cytokines (TNF-α, TGF-β, IFN-γ, IL-4 and IL-10) known to be present in the cervical microenvironment and for which receptors were likely to be present on the tumour cells. None of these influenced CCR4 expression. However, CCR4 mRNA levels, but not protein levels, were up-regulated by co-culture of C-41 cells with macrophages.

CCR4 and D6 are located on chromosome 3p close to where critical cervical cancer tumour suppressor genes are thought to be located with complex aberrations (loss of heterozygosity, homozygosity and gene amplification) reported [25, 26, 27]. While neither CCR4 nor D6 are directly implicated in these changes [26], genetic alterations nearby may have an impact on their regulation.

EBV-immortalised B cells secrete CCL22 as well as CCL3 and CCL4 [28]. Stable expression of the EBV oncogene LMP1 also induced CCL17 and CCL22 in a B cell line and LMP1-induced CCL17 and CCL22 expression was regulated by NF-kB. It was suggested that induction of these two chemokines by EBV helps malignant cells evade immune surveillance by attracting Th2 and Treg cells. Other oncogenic changes may induce CCL17 and CCL22 production by epithelial cells.

The inventors undertook the detailed quantitation of two components of the mononuclear infiltrate in cervical cancer, specifically CD68+ macrophages and FoxP3+ Tregs. The density of CCR4-positive infiltrating cells increases in CIN compared with normal cervix and increases further in both SCC and adenocarcinomas. CD68+ macrophages follow the same pattern and we found that these were CCR4 positive. Cross talk between macrophages and malignant cells is critical at all stages of cancer progression, influencing malignant cell survival, aiding the angiogenic switch, polarizing leucocytes and aiding malignant cell invasion [29,30,31]. In cancers of the cervix and oesophagus, the chemokines CCL17 and CCL22 play a role in macrophage recruitment whereas in other cancers e.g. ovarian cancer, chemokines such as CCL2 are critical [32].

CCL17 and CCL22 are also important in the recruitment of Tregs that increase in a manner parallel to the CD68+ cells in the cervical biopsies. The recruitment of Treg cells to the pre-malignant and malignant lesions fosters immune privilege. For instance, in Hodgkin's Lymphoma, HL, the malignant cells are surrounded by a large number of CCR4+ FoxP3+ lymphocytes [33]. These cells, recruited by the malignant HL cells, create a favourable environment for malignant cells to escape the host immune system. The inventors think that this is also the case for cervical and oesophageal cancer. Hence not only do the changes in CCL17 and CLL22 gradients directly encourage tumor cell survival and spread but they attract in leukocytes that may also provide survival factors for the tumor cells and contribute to immune privilege/immunosuppression that prevents effective host responses against the tumor.

These data demonstrate that the presence of epithelial CCR4 is both a highly sensitive and highly specific biomarker for both pre-malignant and malignant cervical neoplasia. The role of CCR4 expression in cervical cancer progression is, as yet, unclear though the inventors' data suggests that CCR4 may offer cells protection from apoptotic stimuli within the tumour environment as well as being necessary for tumour cell invasion of the basement membrane. Due to its high sensitivity and selectivity, there is the potential for CCR4 to be used as a diagnostic biomarker for all stages of cervical cancer.

Subsequently the inventors also tested for the expression of CCR4 in 31 samples of oesophageal tumours, another tumour type that has a strong link with inflammation. By IHC they found that CCR4 was not detectable in any normal epithelial oesophageal tissue, but was present in epithelial cells of all pre-invasive and invasive lesions. Due to its high sensitivity and selectivity, there is the potential for CCR4 to be used as a diagnostic biomarker for all stages of oesophageal cancer.

In summary, the chemokine receptor CCR4 and its ligands increase during malignant progression of cervical, oesophageal, kidney, brain, ovarian or breast cancers. Changes in CCR4 and gradients of its ligand have several pro-tumor implications. First CCR4 stimulation increases the growth and survival of the initiated and invasive cancer cells; second, changes in chemokine gradients assists in invasion of the basement membrane and subsequent movement of the malignant cells into the blood vessels or lymphatic system. Finally CCL17 and CLL22 attract the types of cells, including M2 macrophages and FoxP3 Tregs that encourage tumor growth and allow the initiated cells to escape immune surveillance. CCR4 and its ligands may be useful diagnostic markers and therapeutic targets in epithelial neoplasia.

The invention is in part described by way of experimental work and examples, in which the following materials and methods were employed:

EXAMPLES

Cervical Tissue Samples and Oesophageal Specimens

For the mRNA studies, fifteen tumour biopsies from patients with cervical cancer (11 squamous cell carcinoma, S1-S11, and 4 adenocarcinomas, A1-A4) and 14 samples of non-neoplastic cervical tissue (N1-N14) were obtained during surgery and snap-frozen in liquid nitrogen. Diagnosis was made by the pathology department of Barts and The London NHS Trust. Patient samples were divided according to the FIGO classification (stage I, II, III, IV) and tumour biopsies were classified according to increasing grade of nuclear atypia (1, 2, 3) or as well, moderately, or poor differentiation.

For immunohistochemistry, paraffin embedded samples (n=166) from 150 different patients were obtained from Barts and The London NHS Trust and the Clinical Centre of Serbia, Belgrade. Access to fresh and paraffin-embedded human samples satisfied the requirements of the East London and City Health Authority Research Ethics Subcommittee (LREC no. T/02/046).

Resected specimens from thirty-one patients with primary squamous oesophageal carcinoma were also included in this paper. These patients were from a high-risk area for oesophageal carcinoma in Anyang City, Henan Province, China. All patients received surgical treatment at the Department of Surgery of the Central Hospital of Anyang. None of these patients had undergone chemotherapy, radiotherapy or immunomodulatory therapy before surgery. Samples were taken from macroscopically cancerous and the corresponding normal areas of the same cancer patient. The tissues were fixed in PBS containing 10% neutral-buffered formalin.

RNA Extraction and RNase Protection Assay (RPA)

Cervical tissue biopsies were homogenised using a liquid nitrogen-cooled mill 6750 (Glen Creston Ltd, Stanmore) and then solubilised in Tri Reagent™ (Sigma, Poole, UK). Extracted RNA was treated with 10 units DNase (Pharmacia, St Albans, UK) following the manufacturers instructions. RPA was performed using Riboquant® hCR5 and hCR6 template sets (BD Pharmingen, Oxford, UK) and [$\alpha^{32}$P] UTP (Amersham International plc, Aylesbury, UK). RNase-protected fragments were run on an acrylamide-urea sequencing gel (BioRad Laboratories Ltd, Hemel Hempstead, UK), adsorbed to filter paper and dried under vacuum. Autoradiography was performed using Kodak Biomax MS film with a Transcreen LE intensifying screen (Sigma).

Microdissection and Gene Array

Paraffin-embedded cervical tissues were cut under RNase-free conditions and mounted onto UV-treated PALM® membrane slides (PALM, Microlaser Technologies, Germany). These were then deparaffinised in xylene and rehydrated through graded alcohols. Samples were stained for 1 min with Mayer's haematoxylin solution, dehydrated and air-dried before processing. Sections were laser-microdissected following the manufacturer's protocol. Briefly, areas of interest were laser microdissected and catapulted into a microfuge cap containing Protein Kinase (PK) buffer. Approximately 500-5000 cells were captured in each session. Laser microdissected cells were dissolved in 100 μl PK Buffer mixed with 5 μl PK. Total RNA was then extracted using the Paraffin block RNA isolation kit (1902, Ambion, USA) according to the manufacturer's instructions. cDNA was amplified as described above and analysed using custom-made microfluidic gene array cards (PE Applied Biosystems) according to the manufacturer's instructions.

The gene expression profile of individual genes in seven cervical tumour samples was compared to five normal cervical samples. The gene expression levels in the normal epithelial or stromal cells samples was used as a baseline value of "1" and was compared with the average value of either tumour epithelial cells or tumour stromal cells respectively. The laser microdissected tumour samples comprised of one sample from stage 1A2 and 2B, and five of stage 1B1.

Immunohistochemistry

Paraffin-embedded sections (4 μm) were stained for CCR4, CCL17 and CCL22. Briefly, sections were dewaxed in xylene and dehydrated through an ethanol gradient. Following PBS washing the antigen was exposed using Target Retrieval Solution (S1700, DAKO) at 95° C. for 20 min or Antigen Unmasking Solution (H-3300, Vector) for 9 min in a microwave. Sections were blocked with normal rabbit or goat serum for 30 min and incubated overnight at 4° C. with the primary antibody: CCR4 (1:300, ab1669, AbCam, Cambridge), CCL17 (1:50, ab9816-50, AbCam, Cambridge) and CCL22 (1:20, 500-P107, Peprotech). Following incubation with a biotinylated secondary antibody (anti-goat or anti-rabbit IgG, 1:200, Vector) for 30 min at room temperature, antigens were revealed with 3,3'-diaminobenzidine (DAB; Sigma). Slides were then counterstained with haematoxylin, dehydrated and mounted. Omission of the primary antibody was used as a negative control. To check specificity of the CCR4 antibody, some CCR4-negative cells were transfected with cDNA for this chemokine receptor. The CCR4 antibody detected surface protein only on the successfully transfected cells.

Double Staining, CD68, FoxP3, SR-A: Scoring Methods and Categories

For assessment of CCR4, CCL17 and CCL22 expression on non-malignant and malignant epithelial cells, each sample was assessed semi-quantitatively with the following scoring system: 0 (no positive protein expression), +1 (<25% of the cross-section on average has positive expression), +2 (26-50%), +3 (51-75%), +4 (>76%). The intensity of positive cells was analysed as follows: 0 (no expression), 1 (mild expression), 2 (moderate expression), 3 (strong expression). Scoring of CCR4, CCL17 and CCL22 expression in tumour stroma (intratumoral infiltrating cells) and the invasive border of the tumour (peritumoral infiltrating cells) was performed based on the 'running mean' method [43]. Necrotic areas were avoided. A total of 15 high-power fields (×400 magnification) were counted. Five scales were set up as follows: 0=no CCR4 protein expression; +1=1-10 CCR4 positive cells per HPF; +2=10-20 positive cells per HPF; +3 (21-30 cells per HPF); +4 (>30 cells). The overall staining result was obtained by calculating 'percentage'×'intensity'. The IHC scoring on tumour and infiltrating cells was performed by a board-certified pathologist (YW).

Cervical Cancer Cell Line Culture

The cervical cancer cell line C-41 (ATCC, Rockville, Md., USA) was cultured in DMEM medium supplemented with 10% FCS. In some experiments cells were stimulated with 1, 10, 100, or 1000 ng/ml of CCL17 or CCL22 (PeproTech, London, UK). Proliferation and migration were assessed using methods described previously [11].

Statistical Analysis

Statistical significance was evaluated using unpaired t-test with Welch's correction (Instat software, San Diego, Calif.). A P value of <0.05 was considered significant.

Experiment 1—Ribonuclease Protection Assay for Chemokine Receptors

Figure 1:
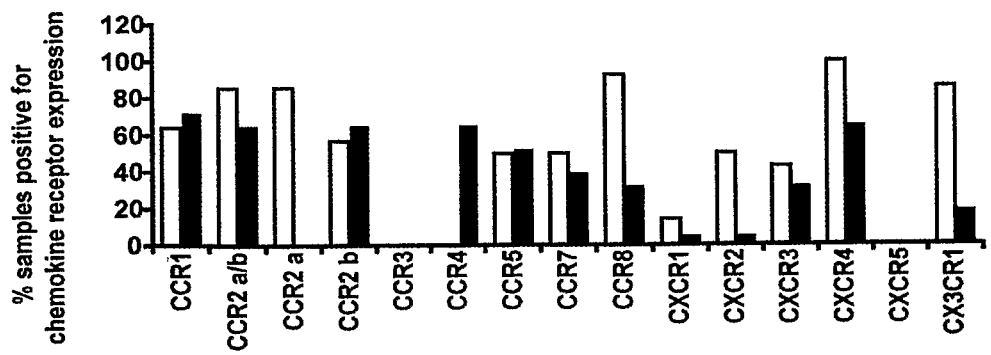
FIG. 1—Expression of CCR4 mRNA is increased in malignant cervical biopsies compared with normal tissues.
Figure 1:
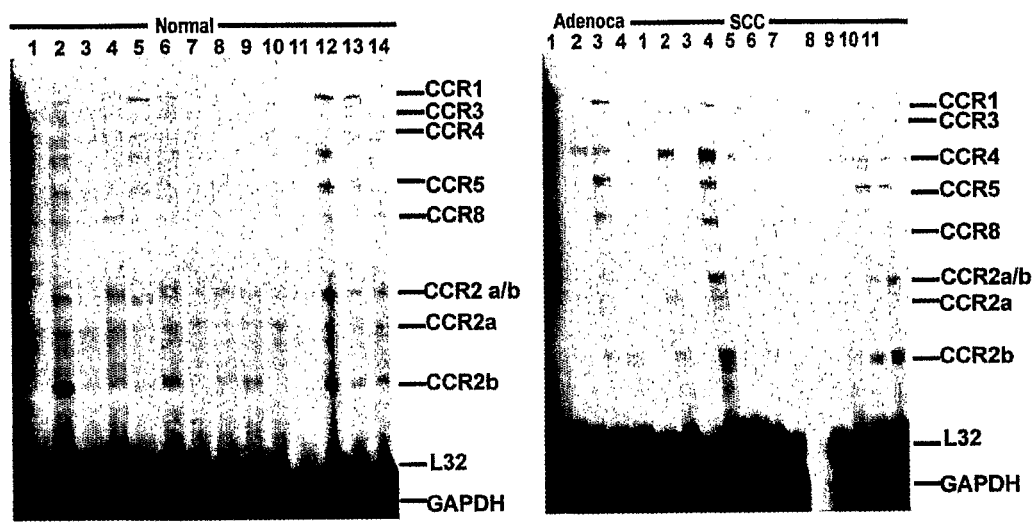
Figure 1:
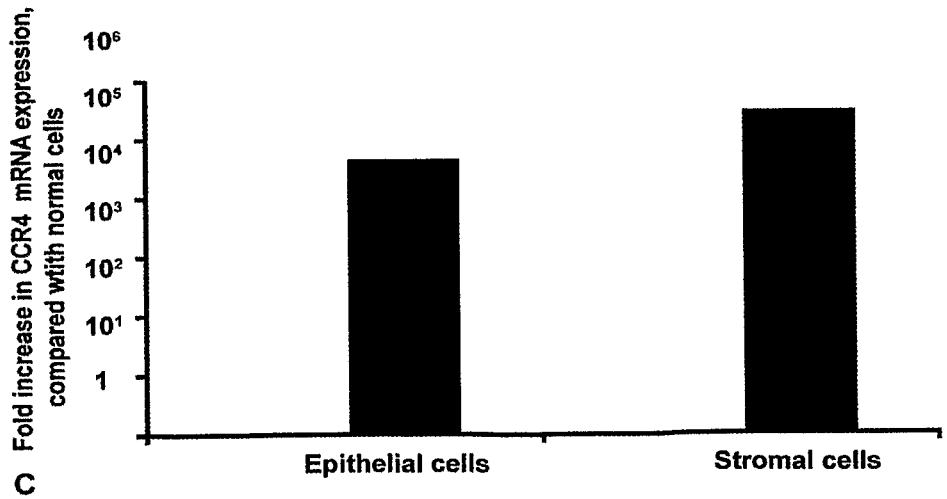

Ribonuclease protection assays (RPA) were used to screen for 13 chemokine receptor mRNAs in fresh-frozen biopsies of human cervical tissue. As can be seen from the summary graph in FIG. 1A, a range of chemokine receptor mRNAs was found in cervical tissue extracts with some discrete differences between the non-neoplastic and the malignant biopsies. Of particular interest was the chemokine receptor CCR4, which was present in the malignant cervix but not in extracts from non-neoplastic cervical biopsies (FIG. 1B).

As chemokine receptor expression was examined on whole tissue extracts containing a mixed population of stromal cells and epithelial cells, we next investigated the cellular source of the CCR4 mRNA. mRNA was extracted from laser microdissected stromal and epithelial cell areas of normal and malignant cervical biopsies, and semi-quantitative Real Time RT-PCR was used to analyse CCR4 expression with 18S rRNA as a control. As shown in FIG. 1C, CCR4 mRNA was up-regulated in stromal areas from malignant tissues when these were compared to their non-neoplastic counterparts. In addition, and unexpectedly, CCR4 mRNA was also up-regulated in extracts from the malignant epithelial cell areas compared to normal epithelium.

To investigate further these observations relating to CCR4 mRNA, we stained a cohort of biopsies for CCR4 using immunohistochemistry, IHC. We assessed CCR4 protein expression in 166 samples of paraffin embedded cervical tissues from 150 different patients: nonneoplastic, n=23; CIN I, n=30; CIN II, n=17; CIN III, n=16; SCC, n=45; recurrent tumour, n=15; lymph node metastasis (LN mets), n=10; adenocarcinoma, n=10. Both leucocytes and epithelial cells expressed CCR4 protein. To quantify our results, an IHC score was calculated by multiplying the 'positivity' and 'intensity' (see the description of methods and FIGS. 8 and 9 for a more details).

Experiment 2—CCR4 Protein is Found on Infiltrating Leucocytes in Human Cervical Biopsies As shown in FIG. 2 (A-C), leucocytes in the stromal areas of the biopsies stained positive for CCR4. The IHC score for CCR4 positivity in the stromal areas is summarised in FIG. 3A (white bars). The non-neoplastic tissues were negative for CCR4 leucocytes (FIGS. 2A, 3A). There were more CCR4 expressing stromal cells in the CIN samples (FIG. 2 B, 3A) and this increased further in the invasive neoplastic cervical samples (FIG. 2 C, 3A). The intensity of CCR4 expression on the infiltrating leucocytes also increased with malignant progression. In non-neoplastic tissues this was mild; intensity was moderate to strong in CIN and adenocarcinomas, and intensity was strong in invasive SCC, recurrent tumours and lymph node metastases (FIG. 8).

The stroma consists of various cell types, and tests were carried out to ascertain which of the infiltrating cells contributed to CCR4 expression. As macrophages and Treg cells express CCR4, CCR4 protein expression was examined in these two cell types and also counted the number of CD68+ macrophages and FoxP3+ Treg cells in the tissue biopsies were counted.

Experiment 3—CCR4 Positive Macrophages Treg Cells Increase with Malignant Progression The number of CD68+ macrophages and FoxP3+ Tregs increased with malignant progression of the cervix. As shown in FIG. 2 D-I there were few CD68 and FoxP3 cells in biopsies of normal cervix, but the numbers increased in CIN and both cell types were prominent in invasive cancers.

The numbers of CD68+ and FoxP3+ cells were then counted in the 122 and 33 biopsies respectively. As shown in FIG. 3B there was a significant (p<0.001) increase in CD68+ cells in CIN lesions compared to normal cervix. The number of 13 CD68+ cells further increased in SCC, adenocarcinoma, recurrent cancers and lymph node metastases (P<0.001, and for LN mets P<0.05, compared to normal cervix). A similar increase in FoxP3+ cells occurred with malignant progression with SCC, adenocarcinomas and lymph node metastases all showing significant increases in the FoxP3+ infiltrate compared to normal cervix (p<0.01).

To study the phenotype of infiltrating CCR4 expressing cells, an assessment was made of cell surface expression of CCR4 by macrophages and Tregs using double immunohistochemical staining for CD68 and FoxP3. This confirmed that CD68+ and FoxP3+ cells also express CCR4 protein (data not shown). A subset of 33 paraffin embedded tissues were also stained for scavenger receptor-A (SR-A) protein (non-neoplastic=10, CIN=10, SCC=10, adenocarcinoma=3). SR-A is a cell surface marker for M2 alternatively activated macrophages [12]. SR-A could not be detected on stromal cells in normeoplastic lesions but in CIN and invasive cancer, a proportion of the CD-68+ cells expressed SR-A (data not shown).

These studies show, firstly, that malignant progression of the cervix is associated with an increase in the numbers of CD68+ macrophages and FoxP3+ Treg cells. These cells could provide pro-tumour growth factors for the malignant cells and also help create an immunosuppressive microenvironment that would help transformed cells evade immune surveillance. Secondly, these results showed that the original observation of an increase in CCR4 mRNA in malignant compared to normal cervical cancer was due, at least in part, to an increased infiltrate of CCR4 expressing leucocytes, including macrophages and Treg cells.

However, the laser microdissection result showed that CCR4 mRNA was also increased in epithelial areas of the tumours, and when assessing CCR4 protein on infiltrating leukocytes, it was clear that the chemokine receptor was also present on some epithelial cells (see FIGS. 2B and C). This was unexpected and warranted further investigation.

Experiment 4—Epithelial Cells in Cervical Biopsies Also Express CCR4

In the non-neoplastic cervical biopsies, normal epithelial cells did not express CCR4 (FIG. 2A). However epithelial cells in over 90% of the CIN cases expressed CCR4 (FIGS. 2B and 2E). 96% of the SCC samples had CCR4-positive epithelial cells (FIGS. 2C and 2F) and epithelial cells 90% of adenocarcinoma samples were positive for CCR4 (FIG. 2G). Malignant epithelial cells in all recurrent tumours and lymph node metastases expressed CCR4 protein. Full details of the IHC results for CCR4 protein on epithelial cells are shown in FIG. 9 and summarised in FIG. 2D (black bars). CCR4 expression was not restricted to a minority of epithelial cells. FIGS. 2E-G and 9 show that the majority of malignant epithelial cells in cervical biopsies of CIN and invasive cancer were CCR4 positive.

More detail relating to the IHC score for different stages of CIN is shown in FIG. 2 H. This shows that epithelial CCR4 expression was essentially unchanged through progression from CINI to III but that stromal levels of CCR4 increased from CIN I-III Experiment 5—Statistical Analysis of CCR4 Expression During Cervical Cancer Progression Statistical analysis of the data in FIGS. 8 and 9 showed that CIN lesions showed a significant up-regulation of CCR4 protein in both epithelial (P=0.0001) and stromal (P=0.0001) compartments when compared to non-neoplastic cervical tissues. CCR4 expression in invasive SCC was also significantly increased in both the epithelial (P=0.0001) and stromal compartments (P=0.0001) when compared to non-neoplastic tissues. Also in adenocarcinoma samples, CCR4 was up-regulated 15 on epithelial (P=0.0006) and stromal cells (P=0.0050) when compared to non-neoplastic cervical tissue.

Experiment 6—CCL22 mRNA and Protein Levels Change with Malignant Expression

In normal tissues, CCL22 is a product of macrophages, monocytes, DC, B and T cells [13, 14]. It is also found in epithelial tissues; for instance intestinal epithelium constitutively produces CCL22 that can be further up-regulated by inflammatory cytokines such as TNF-$\alpha$ [15]. mRNA was isolated from 14 biopsies of normal cervix, 11 SCC and 4 adenocarcinomas and CCL22 levels assessed by real time RT PCR. As shown in FIG. 4A CCL22 mRNA levels were lower in the malignant tissues compared with the normal biopsies but this was not significant (P=0.43). A total of 52 samples of paraffin embedded cervical tissues from 50 different patients were assessed for CCL22 protein: non-neoplastic, n=16; CIN, n=17; SCC, n=19. In all cervical biopsies, CCL22 was detected in the epithelial cells (FIG. 4B-D). Fourteen of 16 normal samples, 15/17 CIN, 14/19 SCC had CCL22 positive epithelial cells. Infiltrating leucocytes in all biopsies contained CCL22 (FIG. 4C, D). The epithelial IHC score declined slightly between the CIN lesions and SCCs (FIG. 4E black bars). However, the stromal score for CCL22 increased from normal to CIN and SCC (FIG. 4E white bars).

Experiment 7—CCL17 mRNA and Protein Levels Change with Malignant Expression

In normal tissues, CCL17 is expressed by vascular and lymphatic endothelial cells but is also produced by macrophages, DC and keratinocytes [16, 17, 55] mRNA was isolated from 14 biopsies of normal cervix, 11 SCC and 4 adenocarcinomas and CCL17 levels assessed by real time RT-PCR. As shown in FIG. 5A levels of CCL17mRNA were higher in SCC compared to normal cervix. A total of 74 samples of paraffin embedded cervical tissues from 70 different patients were assessed for CCL17 protein: non-neoplastic, n=21; CIN, n=33; SCC, n=20. Normal cervical biopsies had low levels of CCL17 in a minority of samples both the epithelium and stroma (FIG. 5B). Only 2/19 normal samples had CCL17 positive cells in the epithelium compared with 23/33 CIN samples and 13/20 SCC. The number of stromal cells that were CCL17 positive was increased in CIN (FIG. 5C) and SCC (FIG. 5D) compared to normal samples. Six of 21 normal biopsies had CCL17 positive stromal cells compared to 25/33 CIN and 15/20 SCC. The epithelial and stromal CCL17 IHC score was increased in CIN and SCC compared to normal biopsies (FIG. 5E). When the IHC scores from individual biopsies were analysed, there was a statistically significant difference in CCL17 IHC score in stroma from CIN (P=0.001) and SCC (P=0.002) compared to normal biopsies.

There was also a difference in the IHC scores in epithelial areas of CIN (P=0.001) and SCC (P=0.009) compared to normal. These data show that chemokine gradients changed with the transition from intraepithelial neoplasia to invasive disease.

Experiment 8—CCR4 is Functional on Cervical Cancer Cells

To investigate the biological significance of CCR4 expression on cervical cancer cells a number of cervical cancer cell lines (CaSki, Me180, Hela-Ohio, Hela-S3, Siha, C33A, C41-1) were screened for CCR4 expression. The cell line C-41 expressed cell surface CCR4 in a constitutive manner (FIG. 6A). Using FACS analysis it was shown that C-41 cells expressed cell surface CCR4. This cell line also had intracellular CCL22 protein but the other CCR4 ligand CCL17 was not present (FIG. 6A). Following stimulation with 100 ng/ml CCL22, cell surface CCR4 protein was internalized on C-41 cells after 2 hours and returned back to the surface after 3 hours (FIG. 6B). Following stimulation with 100 ng/ml CCL17, cell surface CCR4 protein was also internalized on C-41 cells after 2 hours and returned back to the surface after 3 hours (FIG. 6C). C-41 cells demonstrated a typical bell-shaped chemotactic response towards both CCL17 and CCL22 in trans-well migration assays (FIG. 6D). At 10 ng/ml, CCL17 induced significant migration (P=0.036) and also at 100 ng/ml and 1000 ng/ml (P=0.0006 and P=0.0004 respectively). Similar results were seen with CCL22 at 10 ng/ml (P=0.0081), 10 ng/ml (P=0.0009) and at 1000 ng/ml (P=0.0348).

C-41 cells showed increased proliferation after stimulation with either 10 ng/ml (P=0.017) or 100 ng/ml (P=0.044) of CCL17. 1 ng/ml CCL22; (P=0.026), 100 ng/ml CCL22 (P=0.043), but not 10 ng/ml CCL22 (P=0.195), also simulated C-41 cell growth (FIGS. 5C and D). CCR4 was therefore functional on this cervical cancer cell line, suggesting that it may also be functional in vivo.

Experiment 9—CCR4 is Expressed on Epithelial and Stromal Cells During Malignant Progression of the Oesophagus It was unknown as to whether the expression of CCR4 and changes in chemokine ligand were specific for cervical cancer or whether they were seen in any other epithelial malignancies that have a link with inflammation. Cancer of the oesophagus is an epithelial cancer where examples of all stages of neoplastic progression can be readily obtained, often simultaneously from the same patient. CCR4 expression was examined in 31 specimens from patients with oesophageal cancer. In 27 of the cases, all stages of carcinogenesis of the oesophagus: normal, hyperplasia, dysplasia, in situ carcinoma and invasive cancer, were present in biopsies from the same patient. Four of 31 cases had pre-invasive lesions without invasive cancer areas. As shown in FIG. 7A, there was no detectable CCR4 expression in normal epithelial cells of oesophagus, apart from a few CCR4-positive cells around the basal layer of hyperplastic epithelium (FIG. 7B). In 30 of 31 cases CCR4 protein was present on epithelial cells in all stages of pre-invasive lesions (FIG. 7C,D), that the intensity and percentage of CCR4 expressing cells in dysplastic lesions was much higher than in hyperplastic epithelial cells. Epithelial cells in the invasive cancer were also CCR4-positive (FIG. 7H). In some places, there was an abrupt transition between normal and abnormal mucosa FIG. 7C, D). Most interestingly, there were high levels of CCR4 expression in the dysplastic cells, but the cells in the superficial layers, and adjacent normal mucosa were negative. CCR4-positive cells were also present in the stroma, the pattern being the same as in cervical cancer. As shown in FIG. 7E, there were few CCR4-positive cells in the normal submucosa; with malignant progression, there were more CCR4 positive cells infiltrating the stroma (FIG. 7F-H).

Experiment 10—CCL17 and CCL22 in Oesophageal Biopsies

IHC was used to assess CCL17 and CCL22 expression in 23 of the oesophageal samples in which all stages of carcinogenesis were present in each sample. CCL17 was generally absent in both the epithelial and stromal areas of the normal tissues, although there were a few CCL17-positive cells in the stroma and a minority of hyperplastic areas. The number of samples continuing CCL17-positive epithelial or stromal cells increased in dysplasia and was highest in invasive areas with 10/23 of these showing some CCL17 positivity. Of particular note was strong CCL17 immunoreactivity on the endothelial cells or blood/lymphatic vessels in the submucosa of dysplastic but not normal epithelium.

Similar to the observations in cervical cancer, the levels of stromal positivity for CCL22 also increased with malignant progression. Only 1/23 samples showed CCL22 positive cells in the stroma of the normal areas, but in dysplastic areas and invasive areas 20/23 and 18/23 samples respectively contained CCL22-positive cells in the stroma. The stromal cell CCL22 positivity increased with the degree of dysplasia. Eight of 23 dysplasia I samples had CCL22 positive cells in the stroma; this increased to 19 of 23 samples of dysplasia II and 20/23 samples of dysplasia III. There was one difference between the cervical and oesophageal epithelium in that CCL22 was not detected in normal epithelium although it has been reported to be present in normal intestinal epithelium [15]. Epithelial CCL22 expression increased with malignant progression of the oesophagus; 0/23 samples were positive in the normal areas, 2/23 hyperplasias, 7/23 dysplasias and 14/23 invasive areas had CCL22 positive epithelial cells. Finally, more endothelial cells of blood vessels within the stroma of invasive cancer tissues were positive for CCL22 staining compared with normal and dysplastic epithelium.

Experiment 11—The results of a Screen for CCR4 Expression in a Wider Range of Tumours Using a tumour cDNA library (Cancer Research UK) containing cDNA generated from RNA isolated from 5-10 tumour samples and 2-5 normal samples for 11 different tumour types: lung, colon, bladder, stomach, pancreas, skin, breast, brain, oesophagus, ovary and prostate. The CCR4 mRNA expression levels were measured using quantitative Real Time RT-PCR.

CCR4 mRNA levels were significantly elevated in cancers of the cervix, oesophagus, kidney, brain, breast and ovary.

Experiment 12—Analysis of Expression of CCR4 in Cervical and Renal Cancer Cell Lines FIG. 11 shows the results of Fluorescence Activated Cell Scanning (FACS) analysis on cervical (C41, C33A) and renal cancer cell lines using an anti-CCR4 antibody to detect CCR4 expression. All the cell lines expressed CCR4. The dashed lines in FIG. 11 show the data for an isotype-matched control antibody.

Experiment 13—Effects of Common Cytokines on CCR4 Expression by Tumour Cells

The most common cytokines present in a tumour are IL-10, TGF-β, FGF, TNF-α. The C41 cervical cancer cell line was stimulated in culture with different cytokines (IL-10, TNF-α, TGF-β, FGF; 20 ng/ml) for 24 h. The expression of CCR4 was then determined by FACS analysis. As shown in FIG. 12, CCR4 was upregulated in terms of percentage of positive cells after IL-10, TGF-β and FGF stimulation (blue line) when compared with the unstimulated cells (black line). The dashed line shows the data for an isotype control. The bold line shows CCR4 expression after stimulation. The results indicate that tumour microenvironment can induce expression of CCR4 on tumour cells.

REFERENCES

1. Allen, S. J., Crown, S. E., and Handel, T. M. 2006. Chemokine: receptor structure, interactions, and antagonism. *Annu Rev Immunol* 25:787-820.
2. Balkwill, F. R. 2004. Cancer and the chemokine network. *Nature Reviews Cancer* 4:540-550.
3. Muller, A., Homey, B., Soto, H., Ge, N., Catron, D., Buchanan, M. E., McClanahan, T., Murphy, E., Yuan, W., Wagner, S. N., et al. 2001. Involvement of chemokine receptors in breast cancer metastasis. *Nature* 410:50-56.
4. Scotton, C. J., Wilson, J. L., Milliken, D., Stamp, G., and Balkwill, F. R. 2001. Epithelial cancer cell migration: a role for chemokine receptors? *Cancer Res* 61:4961-4965.
5. Zeelenberg, I. S., Ruuls-Van Stalle, L., and Roos, E. 2003. The chemokine receptor CXCR4 is required for outgrowth of colon carcinoma micrometastases. *Cancer Res* 63:3833-3839.
6. Balkwill, F. 2004. The significance of cancer cell expression of CXCR4. *Seminars in Cancer Biology* 14:171-179.
7. Burger, J. A., and Kipps, T. J. 2006. CXCR4: a key receptor in the crosstalk between tumor cells and their microenvironment. *Blood* 107:1761-1767.
8. Zlotnik, A. 2006. Chemokines and cancer. *Int J Cancer* 119:2026-2029.
9. Meijer, J., Zeelenberg, I. S., Sipos, B., and Roos, E. 2006. The CXCR5 chemokine receptor is expressed by carcinoma cells and promotes growth of colon carcinoma in the liver. Cancer Res 66:9576-9582.
10. Letsch, A., Keilholz, U., Schadendorf, D., G., A., Asemissen, A. M., Thiel, E., and Scheibenbogen, C. 2004. Functional CCR9 expression is associated with small intestinal metastasis. *J Invest Dermatol* 122:685-690.
11. Scotton, C. J., Wilson, J. L., Scott, K., Stamp, G., Wilbanks, G. D., Fricker, S., Bridger, G., and Balkwill, F. R. 2002. Multiple actions of the chemokine CXCL12 on epithelial tumor cells in human ovarian cancer. *Cancer Research* 62:5930-5938.
12. Gordon, S. 2003. Alternative activation of macrophages. *Nature Reviews Immunol* 3:23-35.
13. Godiska, R., Chantry, D., Raport, C. J., Sozzani, S., Allavena, P., Leviten, D., Mantovani, A., and Gray, P. W. 1997. Human macrophage-derived chemokine (MDC), a novel chemoattractant for monocytes, monocyte-derived dendritic cells, and natural killer cells. *J Exp Med* 185:1595-1604.
14. Mantovani, A., Gray, P. A., Van Danime, J., and Sozzani, S. 2000. Macrophage-derived chemokine (MDC). *J Leukoc Biol* 68:400-404.
15. Berin, M. C., Dwinell, M. B., Eckmann, L., and Kagnoff, M. F. 2001. Production of MDC/CCL22 by human intestinal epithelial cells. *Am J Physiol Gastrointest Liver Physiol* 280:G1217-G1226.
16. Imai, K., Kobayashi, M., Wang, J., Shinobu, N., Yoshida, H., Hamada, J., Shindo, M., Higashino, F., Tanaka, J., Asaka, M., et al. 1999. Selective secretion of chemoattractants for haemopoietic progenitor cells by bone marrow endothelial cells: a possible role in horning of haemopoietic progenitor cells to bone marrow. *Br J Haematol* 106:905-911.
17. Sallusto, F., Palermo, B., Lenig, D., Miettinen, M, Matikainen, S., Julkunen, I., Forster, R., Burgstahler, R., Lipp, M., and Lanzavecchia, A. 1999. Distinct patterns and kinetics of chemokine production regulate dendritic cell function. *Eur J Immunol* 29:1617-1625.
18. Fra, A. M., Locati, M., Otero, K., Sironi, M., Signorelli, P., Massardi, M. L., Gobbi, M., Vecchi, A., Sozzani, S., and Mantovani, A. 2003. Cutting Edge: Scavenging of inflammatory CC chemokines by the promiscuous putatively silent chemokine receptor D6. *J Immunol* 170:2279-2282.
19. Graham, G. J., and McKimmie, C. S. 2006. Chemokine scavenging by D6: a movable feast? *Trends in Immunol* 27:381-386.
20. Woerner, B. M., Warrington, N. M., Kung, A. L., Perry, A., and Rubin, J. B. 2005. Widespread CXCR4 activation in astrocytomas revealed by phospho-CXCR4-specific antibodies. *Cancer Res* 65:11392-11399.
21. Salvucci, O., Bouchard, A., Baccarelli, A., Deschenes, J., Sauter, G., Simon, R., Bianchi, R., and Basik, M. 2006. The role of CXCR4 receptor expression in breast cancer: a large tissue microarray study. *Br Ca Res & Treat* 97:275-283.
22. Schmid, B. C., Rudas, M., Rezniczek, G. A., Leodolter, S., and Zeillinger, R. 2004. CXCR4 is expressed in ductal carcinoma in situ of the breast and in atypical ductal hyperplasia. *Br Ca Res & Treat* 84:247-250.
23. Pils, D., Pinter, A., Reibenwein, J., Alfanz, A., Horak, P., Schmid, B. C., Hefler, L., Horvat, R., Reinthaller, A., Zeillinger, R., et al. 2007. In ovarian cancer the prognostic influence of HER2/neu is not dependent on the CXCR4/SDF-1 signalling pathway. *Br J Cancer* 96:485-491.
24. Borrello, M. G., Alberti, L., Fischer, A., Degl'innocenti, D., Ferrario, C., Gariboldi, M., Marchesi, F., Allavena, P., Greco, A., Collini, P., et al. 2005. Induction of a proinflammatory program in normal human thyrocytes by the RET/PTC1 oncogene. *PNAS* 102:14825-14830.
25. Braga, E., Senchenko, V., Bazov, I., Loginov, W., Liu, J., Ermilova, V., Kuzubskaya, T., Garkavtseva, R., Mazurenko, N., Kisseljov, F. L., et al. 2002. Critical tumor-suppressor gene regions on chromosome 3p in major human epithelial malignancies: allelotyping and quantitative real-time per. *Int J Cancer* 100:534-541.
26. Senchenko, V., Liu, J., Braga, E., Mazurenko, N., Loginov, W., Seryogin, Y., Bazov, I., Protopopov, A., Kisseljov, F. L., Kashuba, V., et al. 2003. Deletion mapping using quantitative real-time PCR identifies two distinct 3-21.3 regions affected in most cervical carcinomas. Oncogene 22:2984-2992.
27. Acevedo, C. M., Henriquez, M., Emmert-Buck, M. R., and Chuaqui, R. F. 2002. Loss of heterozygosity on chromosome arms 3p and 6q in microdissected 33 adenocarcinomas of the uterine cervix and adenocarcinoma in situ. Cancer 94:793-802.
28. Nakayama, T., Hieshima, K., Nagakubo, D., Sato, E., Kakayama, M., Kawa, K., and Yoshie, 0.2004. Selective induction of Th2-attracting chemokines CCL17 and CCL22 in human B cells by latent membrane protein 1 of Epstein-Barr virus. *J Virol* 78:1665-1674.
29. Balkwill, F., Charles, K. A., and Mantovani, A. 2005. Smoldering and polarized inflammation in the initiation and promotion of malignant disease. *Cancer Cell* 7:211-217.
30. Hagemann, T., Wilson, J., Burke, F., Kulbe, H., Li, N. F., Pluddemann, A., Charles, K., Gordon, S., and Balkwill, F. R. 2006. Ovarian cancer cells polarize macrophages toward a tumor-associated phenotype. *J Immunol* 176:5023-5032.
31. Condeelis, J., and Pollard, J. W. 2006. Macrophages: obligate partners for tumor cell migration, invasion, and metastasis. Cell 124:263-266.

32. Negus, R. P. M., Stamp, G. W. H., Relf, M. G., Burke, F., Malik, S. T. A., Bernasconi, S., Allavena, P., Sozzani, S., Mantovani, A., and Balkwill, F. R. 1995. The detection and localization of monocyte chemoattractant protein-1 (MCP-1) in human ovarian cancer. *J Clin Invest* 95:2391-2396.
33. Ishida, T., Ishii, T., Inagaki, A., Yano, H., Komatsu, H., Iida, S., Inagaki, H., and Ueda, R. 2006. Specific recruitment of CC chemokine receptor 4-positive regulatory T cells in Hodgkin lymphoma fosters immune privilege. *Cancer Res* 66:5716-5722.
34. Nakamura, E. S., Koizumi, K., Kobayashi, R., Saitoh, Y., Arita, Y., Nakayama, T., Sakurai, H., Yoshie, O., and Saiki, I. 2006. RANKL-induced CCL22/macrophage-derived chemokine produced from osteoclasts potentially promotes the bone metastasis of lung cancer expressing its receptor CCR4. *Clin Exp Metastasis* July 5.
35. Ishida, T., Inagaki, H., Utsunomiya, A., Takatsuka, Y., Komatsu, H., Iida, S., Takeuchi, G., Eimoto, T., Nakamura, S., and Ueda, R. 2004. CXC chemokine receptor 3 and CC chemokine receptor 4 expression in T-cell and NK-cell lymphomas with special reference to clinicopathological significance for peripheral T-cell lymphoma, unspecified. *Clin Cancer Res* 10:5494-5500.
36. Ishida, T., and Ueda, R. 2006. CCR4 as a novel molecular target for immunotherapy of cancer. *Cancer Sci* 97:1139-1146.
37. Ishida, T., Iida, S., Akatsuka, Y., Ishii, T., Miyazaki, M., Komatsu, H., Inagaki, H., Okada, N., Fujita, T., Shitara, K., et al. 2004. The CC chemokine receptor 4 as a novel specific molecular target for immunotherapy in adult T cell leukemia/lymphoma. *Clin Cancer Res* 10:7529-7539.
38. Kleeff J, Kusama T, Rossi D L, Ishiwata T, Maruyama H, Friess H, Büchler M W, Zlotnik A, Korc M. Detection and localization of Mip-3alpha/LARC/Exodus, a macrophage proinflammatory chemokine, and its CCR6 receptor in human pancreatic cancer. Int J. Cancer. 1999 May 17; 81(4):650-7.
39. Kimsey T F, Campbell A S, Albo D, Wilson M, Wang T N. Co-localization of macrophage inflammatory protein-3alpha (Mip-3alpha) and its receptor, CCR6, promotes pancreatic cancer cell invasion. Cancer J. 2004 November-December; 10(6):374-80.
40. Jöhrer K, Zelle-Rieser C, Perathoner A, Moser P, Hager M, Ramoner R, Gander H, Hölte L, Bartsch G, Greil R, Thurnher M. Up-regulation of functional chemokine receptor CCR3 in human renal cell carcinoma. Clin Cancer Res. 2005 Apr. 1; 11(7):2459-65.
41. Ferenczi, K., Fuhlbrigge, R. C., Pinkus, J. L., Pinkus, G. S. & Kupper, T. S. Increased CCR4 expression in cutaneous T cell lymphoma. *J Invest Dermatol* 119, 1405-1410 (2002).
42. Baatar, D., Olkhanud, P., Newton, D., Sumitomo, K. & Biragyn, A. CCR4-expressing T cell tumors can be specifically controlled via delivery of toxins to chemokine receptors. *J Immunol* 179, 1996-2004 (2007).
43. Nagtegaal I D, Marijnen C A, Kranenbarg E K, Mulder-Stapel A, Hermans J, van de Velde CJ, van Krieken J H. Local and distant recurrences in rectal cancer patients are predicted by the nonspecific immune response; specific immune response has only a systemic effect—a histopathological and immunohistochemical study. *BMC ital Cancer.* 2001; 1:7. Epub 2001 Jul. 16.
44. Libura J, Drukala J, Majka M, Tomescu O, Navenot J M, Kucia M, Marquez L, Peiper S C, Barr F G, Janowska-Wieczorek A, Ratajczak M Z. "CXCR4-SDF-1 signalling is active in rhabdomyosarcoma cells and regulates locomotion, chemotaxis, and adhesion." Blood. 2002 Oct. 1; 100 (7):2597-606.
45. Bange, J; Zwick E, Ullrich A. (2001). "Molecular targets for breast cancer therapy and prevention". Nature Medicine 7: 548-552
46. Ménard, S; Pupa S M, Campiglio M, Tagliabue E (2003). "Biologic and therapeutic role of HER2 in cancer". Oncogene 22: 6570-6578
47. Kute, T; Lack C M, Willingham M, Bishwokama B, Williams H, Barrett K, Mitchell T, Vaughn JP (2004). "Development of herceptin resistance in breast cancer cells". Cytometry 57A: 86-93.
48. Vestergaard C, Bang K, Gesser B, Yoneyama H, Matsushima K, Larsen C G. A Th2 chemokine, TARC, produced by keratinocytes may recruit CLA+CCR4+ lymphocytes into lesional atopic dermatitis skin. J Invest Dermatol. 2000 October; 115(4):640-6.

The invention claimed is:

1. A method of analysis comprising the steps of:
obtaining an oesophagus tumour sample taken from a tumour of a patient; and,
measuring, using an anti-CCR4 antibody, the amount and/or activity of chemokine receptor CCR4 expressed by epithelial tumour cells in the sample and comparing the amount and/or activity of CCR4 expressed by said epithelial tumor cells in said tumour sample with a reference amount and/or activity of CCR4.

2. A method as claimed in claim 1, wherein the reference amount and/or level of activity of CCR4 is an amount and/or activity measured in nonmalignant epithelial cells of one or more non-tumour samples.

3. A method as claimed in claim 2, wherein the, or at least one, non-tumour sample is taken from the patient.

4. A method as claimed in claim 2, wherein the one or more non-tumour samples are not taken from the patient.

5. A method as claimed in claim 1, wherein the measured amount and/or activity of chemokine receptor CCR4 expressed by the epithelial tumour cells is used to predict whether said tumour of the patient will be susceptible to an anti-cancer treatment.

6. A method as claimed in claim 1, wherein the patient receives an anti-cancer treatment and measurements of the amount and/or activity of CCR4 expressed by said epithelial tumor cells in said tumour sample of the patient are made before and after the start of treatment, wherein reduced CCR4 expression and/or activity after treatment compared to prior to treatment indicates the patient has responded to the treatment.

7. A method as claimed in claim 5, wherein the measured amount and/or activity is used in diagnosis of an oesophagus tumour as a malignant tumor.

8. A method as claimed in claim 5, wherein the measured amount and/or activity is used to stage an oesophagus tumour.

9. A method as claimed in claim 5, wherein the anti-cancer treatment comprises an agent which modulates or inhibits CCR4 expression or activity.

10. A method as claimed in claim 9, wherein the agent which modulates or inhibits CCR4 expression or activity is:
(i) an antibody which binds to CCR4; or
(ii) an antibody which binds to CCR4 ligands CCL17 or CCL22; or
(iii) a CCR4 antagonist.

11. A method of treating a cancer patient having an oesophagus tumour expressing CCR4, comprising administering an effective amount of an agent which modulates or inhibits CCR4 expression or activity.

12. A method as claimed in claim 11, wherein the agent which modulates or inhibits CCR4 expression or activity is:
(i) an antibody which binds to CCR4; or
(ii) an antibody which binds to CCR4 ligands CCL17 or CCL22; or
(iii) a CCR4 antagonist.

13. A method of screening for an anti-cancer agent active against an oesophagus tumour which expresses chemokine receptor CCR4 comprising the steps of:
(i) providing test epithelial cells from an oesophagus tumour, wherein the test cells express CCR4 and are capable of, or are in the process of exhibiting a biological activity selected from (a) proliferation, (b) migration, (c) secretion of a protein or a signaling molecule, or (d) cell survival when cultured under specified conditions;
(ii) detecting expression of CCR4 by said test cells,
(iii) exposing the test cells to a candidate agent for a period of time, and
(iv) measuring the biological activity of the test cells, whereby no biological activity or biological activity which is less than the expected activity of such test cells in the absence of candidate agent identifies an anti-cancer agent.

14. A method as claimed in claim 13, wherein a control aliquot of test cells is not exposed to the candidate agent and the biological activity of the control cells is measured so that the expected biological activity is determined.

15. A method as claimed in claim 13, wherein the biological activity of the test cells and any control cells is induced by the addition of a ligand of the CCR4 receptor.

16. A method as claimed in claim 14, wherein the biological activity of the test cells and any control cells is induced by the addition of a ligand of the CCR4 receptor.

17. The method of claim 15, wherein the ligand of the CCR4 receptor is CCL17 and/or CCL22.

18. The method of claim 16, wherein the ligand of the CCR4 receptor is CCL17 and/or CCL22.

* * * * *

SEQUENCE LISTING

```
<160> NUMBER OF SEQ ID NOS: 1

<210> SEQ ID NO 1
<211> LENGTH: 1083
<212> TYPE: DNA
<213> ORGANISM: Artificial
<220> FEATURE:
<223> OTHER INFORMATION: Synthetic DNA showing a cDNA sequence of CCR4.

<400> SEQUENCE: 1
atgaacccca cggatatagc agataccacc ctcgatgaaa gcatatacag caattactat        60
ctgtatgaaa gtatccccaa gccttgcacc aaagaaggca tcaaggcatt tggggagctc       120
ttcctgcccc cactgtattc cttggttttt gtatttggtc tgcttggaaa ttctgtggtg       180
gttctggtcc tgttcaaata caagcggctc aggtccatga ctgatgtgta cctgctcaac       240
cttgccatct cggatctgct cttcgtgttt tccctccctt ttggggcta ctatgcagca       300 gaccagtggg tttttgggct aggtctgtgc aagatgattt cctggatgta cttggtgggc       360
ttttacagtg gcatattctt tgtcatgctc atgagcattg atagatacct ggcgatagtg       420
```

```
                                            -continued
cacgcggtgt tttccttgag ggcaaggacc ttgacttatg gggtcatcac cagtttggct    480
acatggtcag tggctgtgtt cgcctccctt cctggctttc tgttcagcac ttgttatact    540
gagcgcaacc atacctactg caaaaccaag tactctctca actccacgac gtggaaggtt    600
ctcagctccc tggaaatcaa cattctcgga ttggtgatcc ccttagggat catgctgttt    660
tgctactcca tgatcatcag gaccttgcag cattgtaaaa atgagaagaa gaacaaggcg    720
gtgaagatga tctttgccgt ggtggtcctc ttccttgggt tctggacacc ttacaacata    780
gtgctcttcc tagagaccct ggtggagcta gaagtccttc aggactgcac ctttgaaaga    840
tacttggact atgccatcca ggccacagaa actctggctt ttgttcactg ctgccttaat    900
cccatcatct acttttttct gggggagaaa tttcgcaagt acatcctaca gctcttcaaa    960
acctgcaggg gcttttttgt gctctgccaa tactgtgggc tcctccaaat ttactctgct   1020
gacaccccca gctcatctta cacgcagtcc accatggatc atgatcttca tgatgctctg   1080
tag                                                                 1083
```